(12) United States Patent
Mizukura et al.

(10) Patent No.: US 11,216,941 B2
(45) Date of Patent: Jan. 4, 2022

(54) MEDICAL IMAGE PROCESSING APPARATUS, MEDICAL IMAGE PROCESSING METHOD, AND PROGRAM

(71) Applicant: Sony Corporation, Tokyo (JP)

(72) Inventors: Takami Mizukura, Kanagawa (JP); Koji Kashima, Kanagawa (JP)

(73) Assignee: SONY CORPORATION, Tokyo (JP)

(*) Notice: Subject to any disclaimer, the term of this patent is extended or adjusted under 35 U.S.C. 154(b) by 69 days.

(21) Appl. No.: 16/338,692

(22) PCT Filed: Oct. 20, 2017

(86) PCT No.: PCT/JP2017/037969
§ 371 (c)(1),
(2) Date: Apr. 1, 2019

(87) PCT Pub. No.: WO2018/084003
PCT Pub. Date: May 11, 2018

(65) Prior Publication Data
US 2020/0043160 A1 Feb. 6, 2020

(30) Foreign Application Priority Data
Nov. 4, 2016 (JP) .............................. JP2016-216179

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/1128* (2013.01); *A61B 6/461* (2013.01);
(Continued)

(58) Field of Classification Search
CPC ... A61B 1/043; A61B 1/00009; A61B 1/0005; A61B 5/1128; A61B 6/5211;
(Continued)

(56) References Cited

U.S. PATENT DOCUMENTS

| 5,749,830 A | * | 5/1998 | Kaneko | ............... A61B 1/00082 348/E5.038 |
| 7,307,766 B2 | * | 12/2007 | Huang | ..................... H04N 1/56 358/1.9 |

(Continued)

FOREIGN PATENT DOCUMENTS

| JP | 2007-313171 A | 12/2007 |
| JP | 2011-104011 A | 6/2011 |

(Continued)

OTHER PUBLICATIONS

Gunes, "Optimizing the color-to-grayscale conversion for image classification," Oct. 29, 2015, Springer-Verlag (Year: 2015).*

(Continued)

*Primary Examiner* — Alex Kok S Liew
(74) *Attorney, Agent, or Firm* — Xsensus LLP

(57) ABSTRACT

The present technology relates to a medical image processing apparatus, a medical image processing method, and a program that permit superimposition of images at an appropriate mixing ratio without deletion of detailed information. An acquisition section, a superimposition ratio calculation section, and a superimposition processing section are included. The acquisition section acquires a normal frame captured with normal light irradiated on a subject and a special frame captured with special light irradiated on the subject. The superimposition ratio calculation section calculates, on the basis of an intensity value of the special frame, a superimposition ratio indicating a ratio at which the normal frame and the special frame are superimposed. The superimposition processing section performs a superimpo- (Continued)

sition process of superimposing the normal frame and the special frame on the basis of the superimposition ratio. The present technology is applicable to an image processing apparatus for medical use.

14 Claims, 23 Drawing Sheets

(51) Int. Cl.
*A61B 5/11* (2006.01)
*A61B 6/00* (2006.01)
*G06T 1/00* (2006.01)

(52) U.S. Cl.
CPC .......... *A61B 6/469* (2013.01); *A61B 6/5211* (2013.01); *G06T 1/0007* (2013.01); *G06T 2207/30004* (2013.01)

(58) Field of Classification Search
CPC .......... A61B 3/102; A61B 5/0013; A61B 2562/0233; A61B 8/13; A61B 1/0669; A61B 1/00006; G06T 7/0012; G06T 2207/30004; G06T 7/0014; G06T 7/586; G06T 7/90; G06T 7/11; G06T 7/136; G06T 2207/30148; G06T 7/0006; G06T 7/001; G06T 1/0085; G06T 2207/10016; G06T 5/003; G06T 2201/0051; G06T 2207/10116; G06T 2207/20192; G06T 2207/20221; G06T 1/0021; G06T 2201/0061; G06T 2207/20021; G06T 2207/20061; G06T 2207/20092; G06T 5/002; G06T 5/50; G06T 7/12; G06T 11/00; G06T 1/0028; G16H 30/40; G16H 40/63; G01B 2290/45; G01P 5/26; G01S 15/8993; G01N 15/1475; G01N 21/9501; G01N 21/956; G01N 25/72; G01N 21/9054; G01N 21/9081; G01N 21/909; G01J 3/508; H04N 2005/2255; H04N 1/4092; H04N 1/4074; H04N 1/58; H04N 1/6027; H04N 21/2547; H04N 21/41407; H04N 21/41415; H04N 21/4223; H04N 21/4318; H04N 21/43637; H04N 21/6175; H04N 21/654; G02B 21/244
USPC ........ 382/103, 128, 131, 132, 154; 600/103, 600/180, 178, 182; 348/65, 68, 241
See application file for complete search history.

(56) References Cited

U.S. PATENT DOCUMENTS

| | | | | |
|---|---|---|---|---|
| 2002/0026099 A1* | 2/2002 | Adachi | ............. | A61B 5/0071 600/178 |
| 2002/0138008 A1* | 9/2002 | Tsujita | ............. | A61B 1/05 600/473 |
| 2006/0100528 A1* | 5/2006 | Chan | ............. | G01P 5/26 600/476 |
| 2009/0306478 A1* | 12/2009 | Mizuyoshi | ............. | H01S 5/005 600/178 |
| 2009/0318815 A1* | 12/2009 | Barnes | ............. | A61B 5/0064 600/473 |
| 2010/0245616 A1* | 9/2010 | Yoshino | ............. | A61B 1/0646 348/223.1 |
| 2011/0237895 A1* | 9/2011 | Yoshida | ............. | A61B 1/0684 600/180 |
| 2012/0013773 A1* | 1/2012 | Yoshino | ............. | G06T 7/32 348/241 |
| 2012/0154567 A1* | 6/2012 | Yamaguchi | ............. | A61B 1/0653 348/68 |
| 2012/0157775 A1* | 6/2012 | Yamaguchi | ............. | A61B 5/14551 600/180 |
| 2013/0096376 A1* | 4/2013 | Takei | ............. | A61B 1/063 600/103 |
| 2013/0261427 A1* | 10/2013 | Oishi | ............. | G06T 7/0012 600/407 |
| 2013/0307863 A1* | 11/2013 | Waki | ............. | G06T 7/0012 345/589 |
| 2014/0152790 A1* | 6/2014 | Saito | ............. | A61B 1/0005 348/68 |
| 2015/0036803 A1* | 2/2015 | Kuroki | ............. | A61B 6/463 378/98.5 |
| 2015/0238086 A1* | 8/2015 | Saito | ............. | A61B 1/0638 600/339 |
| 2016/0063697 A1* | 3/2016 | Yokota | ............. | G06T 7/344 382/131 |
| 2016/0073927 A1* | 3/2016 | Akimoto | ............. | A61B 1/00009 600/109 |
| 2016/0077008 A1* | 3/2016 | Takasu | ............. | A61B 1/0005 348/77 |
| 2020/0098104 A1* | 3/2020 | Kashima | ............. | A61B 1/06 |

FOREIGN PATENT DOCUMENTS

| | | |
|---|---|---|
| JP | 2011-194040 A | 10/2011 |
| JP | 2011194111 A | 10/2011 |
| JP | 2012-24283 A | 2/2012 |
| JP | 5184016 B2 | 4/2013 |
| JP | 5451956 B2 | 3/2014 |
| JP | 2015095890 A | 5/2015 |
| WO | WO-2008111180 A | 9/2008 |
| WO | 2011/111619 A1 | 9/2011 |

OTHER PUBLICATIONS

International Search Report dated Dec. 26, 2017 for PCT/JP2017/037969 filed on Oct. 20, 2017, 9 pages including English Translation.

* cited by examiner

MEDICAL IMAGE PROCESSING APPARATUS, MEDICAL IMAGE PROCESSING METHOD, AND PROGRAM

CROSS-REFERENCE TO RELATED APPLICATIONS

The present application is based on PCT filing PCT/JP2017/037969, filed Oct. 20, 2017 which claims priority to JP 2016-216179 filed Nov. 4, 2016, the entire contents of each are incorporated herein by reference.

TECHNICAL FIELD

The present technology relates to a medical image processing apparatus, a medical image processing method, and a program and relates, for example, to a medical image processing apparatus, a medical image processing method, and a program that permit a normal image captured with normal light such as white light irradiated on a human body and a special image representing positions of blood vessels acquired with special light irradiated to be combined and a combined image to be displayed.

BACKGROUND ART

Various technologies have been proposed to date for combining a normal image of organs captured with an endoscope with a special image representing positions of blood vessels and lesions such as tumors that are difficult to distinguish in the normal image and displaying a combined image.

For example, PTL 1 describes capture of normal and special images in a time-divided manner. Also, for example, PTL 2 describes combined display of normal and special images.

Here, a normal image refers to an image captured with normal light irradiated, for example, on an organ, a subject. A special image refers to an image captured with special light having a given wavelength different from that of the normal light irradiated. It should be noted that when a special image is captured, a fluorescence agent that reacts to irradiated special light is mixed or applied to blood vessels (blood) or lesions, a subject.

CITATION LIST

Patent Literature

[PTL 1]
Japanese Patent Laid-Open No. 2007-313171
[PTL 2]
Japanese Patent Laid-Open No. 2012-24283
[PTL 3]
Japanese Patent No. 5451956
[PTL 4]
Japanese Patent No. 5184016

SUMMARY

Technical Problem

In a case where a superimposed image is generated simply by adding a normal image and a special image together, there is a region where a signal becomes saturated, in other words, there is a region where a signal exceeds a maximum value that can be taken on by a digital signal value. As a result, there has been a possibility that a poorly visible image deprived, in particular, of detailed information included in a special image may be produced.

Also, in a case where a normal image and a special image are superimposed in such a manner as to ensure that the signal remains unsaturated, for example, in a case where a normal image and a special image are superimposed at a given mixing ratio, there is a possibility that a normal image including peripheral information (e.g., information regarding a periphery of an affected site) may become dark, possibly resulting in an image deprived of detailed peripheral information.

The present technology has been devised in light of such circumstances, and it is an object of the present technology to allow for superimposition of a normal image and a special image at an appropriate mixing ratio.

Solution to Problem

A medical image processing apparatus of an aspect of the present technology includes an acquisition section, a superimposition ratio calculation section, and a superimposition processing section. The acquisition section acquires a normal frame captured with normal light irradiated on a subject and a special frame captured with special light irradiated on the subject. The superimposition ratio calculation section calculates, on a basis of an intensity value of the special frame, a superimposition ratio indicating a ratio at which the normal frame and the special frame are superimposed. The superimposition processing section performs a superimposition process of superimposing the normal frame and the special frame on a basis of the superimposition ratio.

A medical image processing method of an aspect of the present technology includes a step in which a normal frame captured with normal light irradiated on a subject and a special frame captured with special light irradiated on the subject are acquired, a step in which a superimposition ratio indicating a ratio at which the normal frame and the special frame are superimposed, is calculated on a basis of an intensity value of the special frame, and a step in which a superimposition process of superimposing the normal frame and the special frame is performed on a basis of the superimposition ratio.

A program of an aspect of the present technology causes a computer to perform processes including a step in which a normal frame captured with normal light irradiated on a subject and a special frame captured with special light irradiated on the subject are acquired, a step in which a superimposition ratio indicating a ratio at which the normal frame and the special frame are superimposed, is calculated on a basis of an intensity value of the special frame, and a step in which a superimposition process of superimposing the normal frame and the special frame is performed on a basis of the superimposition ratio.

In the medical image processing apparatus, the medical image processing method, and the program, a normal frame captured with normal light irradiated on a subject and a special frame captured with special light irradiated on the subject are acquired, and a superimposition ratio indicating a ratio at which the normal frame and the special frame are superimposed is calculated on the basis of an intensity value of the special frame, and a superimposition process of superimposing the normal frame and the special frame is performed on the basis of the superimposition ratio.

It should be noted that the medical image processing apparatus may be an independent apparatus or an internal block included in a single apparatus.

Also, the program can be provided by being transported via a transport medium or by recorded on a recording medium.

Advantageous Effect of Invention

According to an aspect of the present technology, it is possible to superimpose a normal image and a special image at an appropriate mixing ratio.

It should be noted that the effects described herein are not necessarily limited and may be any of the effects described in this disclosure.

DESCRIPTION OF EMBODIMENT

A description will be given below of a mode for carrying out the present technology (hereinafter referred to as an embodiment).

<Configuration of Endoscopic System>

The technology according to the present disclosure is applicable to a variety of products. For example, the technology according to the present disclosure may be applied to an endoscopic surgical system. Also, although a description will be given by taking an endoscopic surgical system, for example, the present technology is applicable to a surgical system, a microsurgical system, and so on.

Figure 1:
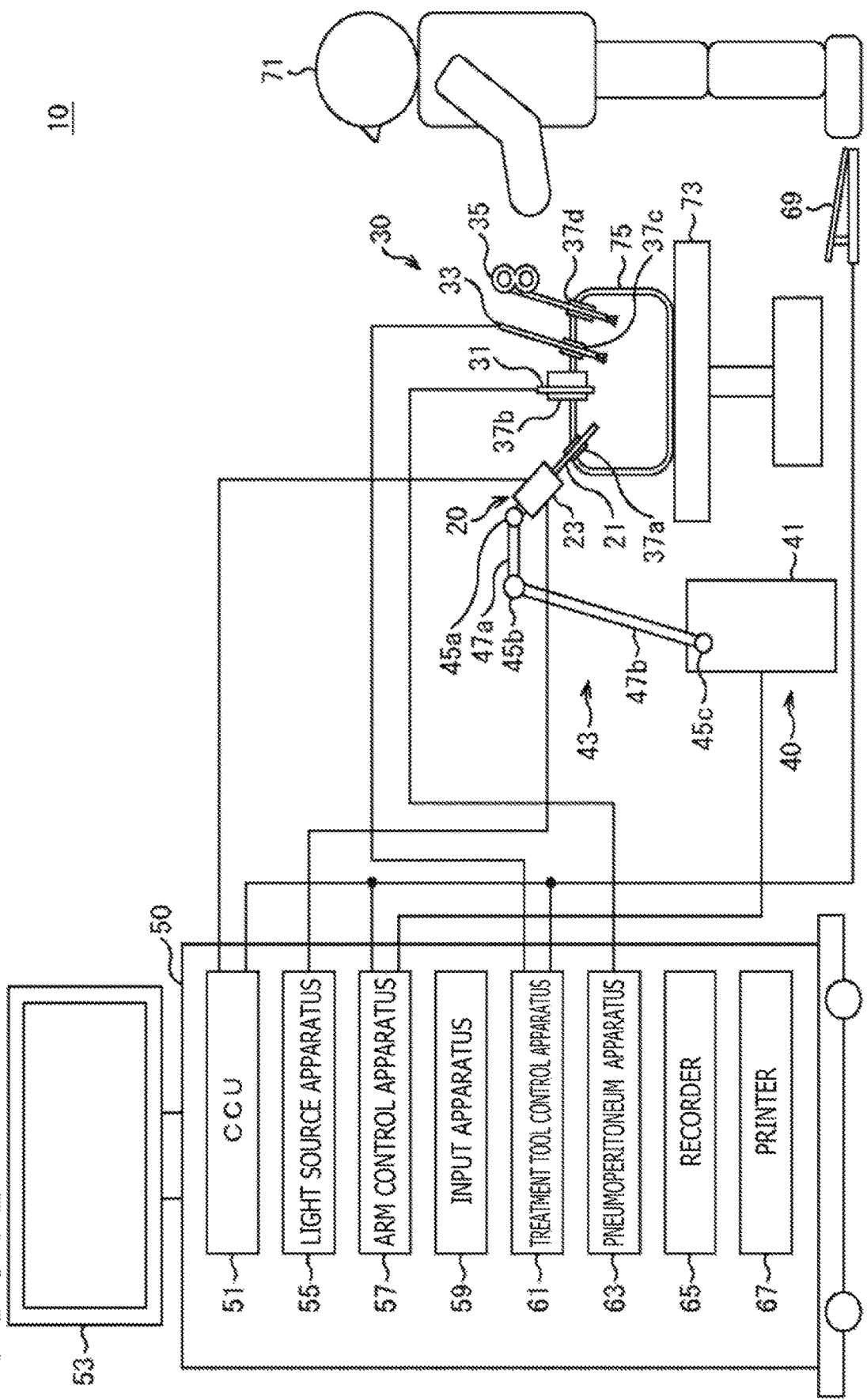
FIG. 1 is a diagram illustrating a configuration of an embodiment of an endoscopic surgical system to which the present technology is applied.

FIG. 1 is a diagram illustrating an example of a schematic configuration of an endoscopic surgical system 10 to which the technology according to the present disclosure is applied. FIG. 1 illustrates the manner in which a practitioner (medical doctor) 71 is operating on a patient 75 on a patent bed 73 by using the endoscopic surgical system 10. As illustrated, the endoscopic surgical system 10 includes an endoscope 20, other surgical tools 30, a support arm apparatus 40 for supporting the endoscope 20, and a cart 50 loaded with variety of apparatuses for endoscopic surgery.

In endoscopic surgery, a plurality of cylindrical specula called trocars 37a to 37d are stuck into an abdominal wall instead of cutting the abdominal wall for laparotomy. Then, a lens barrel 21 of the endoscope 20 and other surgical tools 30 are inserted into a body cavity of the patient 75 through the trocars 37a to 37d. In the example illustrated, a pneumoperitoneum tube 31, an energy treatment tool 33, and forceps 35 are inserted in the body cavity of the patient 75 as the surgical tools 30. Also, the energy treatment tool 33 is a treatment tool for incising and separating a tissue, sealing a blood vessel by means of a high frequency current or ultrasonic vibration. It should be noted, however, that the surgical tools 30 illustrated are merely examples, and a variety of surgical tools commonly used in endoscopic surgery may be used such as tweezers and retractor as the surgical tools 30, for example.

An image of an area to be operated on in the body cavity of the patient 75 shot by the endoscope 20 is displayed on a display apparatus 53. The practitioner 71 gives treatment such as excising an affected area by using the energy treatment tool 33 and the forceps 35 while watching, in real time, the image of the area to be operated on displayed on the display apparatus 53, for example. It should be noted that the pneumoperitoneum tube 31, the energy treatment tool 33, and the forceps 35 are supported by the practitioner 71, an assistant or other person in operation.

(Support Arm Apparatus)

The support arm apparatus 40 includes an arm section 43 that extends from a base section 41. In the example illustrated, the arm section 43 includes joint sections 45a, 45b, and 45c and links 47a and 47b and is driven under control of an arm control apparatus 57. The endoscope 20 is supported and its position and attitude are controlled by the arm section 43. This makes it possible to realize fastening of the endoscope 20 at a stable position.

(Endoscope)

The endoscope 20 includes the lens barrel 21 whose given length from a tip thereof is inserted into the body cavity of the patient 75 and a camera head 23 connected to a base end of the lens barrel 21. Although, in the example illustrated, the endoscope 20 configured as a so-called rigid endoscope having the rigid lens barrel 21 is illustrated, the endoscope 20 may be configured as a flexible endoscope having the flexible lens barrel 21.

An opening portion into which an objective lens is fitted is provided at the tip of the lens barrel 21. A light source apparatus 55 is connected to the endoscope 20, and light produced by the light source apparatus 55 is guided to the tip of the lens barrel by a light guide that extends inside the lens barrel 21 and irradiated on an observation target in the body cavity of the patient 75 via the objective lens. It should be noted that the endoscope 20 may be a forward-viewing endoscope, a forward-oblique-viewing endoscope, or a side-viewing endoscope.

An optics and an imaging element are provided in the camera head 23, and reflected light (observation light) from an observation target is converged by the optics on the imaging element. Observed light is converted into an electric current by the imaging element, thereby generating an electric signal proportional to the observed light, i.e., an image signal proportional to an observation image. The image signal is sent to a camera control unit (CCU) 51 as RAW data. It should be noted that the camera head has a function to adjust a magnification ratio and a focal distance by driving the optics as appropriate.

It should be noted that a plurality of imaging elements may be provided in the camera head 23, for example, to support stereopsis (3D display). In this case, a plurality of relay optics are provided in the lens barrel 21 to guide observed light to each of the plurality of imaging elements.
(Variety of Apparatuses Loaded on Cart)

The CCU 51 includes a CPU (Central Processing Unit), a GPU (Graphics Processing Unit), or other unit and integrally controls the operation of the endoscope 20 and the display apparatus 53. Specifically, the CCU 51 performs various image processing procedures for displaying an image based on the image signal on the image signal received from the camera head 23 such as development process (demosaicing process), for example. The CCU 51 provides an image signal subjected to the image processing procedures to the display apparatus 53. Also, the CCU 51 sends a control signal to the camera head 23 to control the driving thereof. The control signal can include information regarding imaging conditions such as magnification ratio and focal distance.

The display apparatus 53 displays, under control of the CCU 51, an image based on the image signal that has been subjected to image processing procedures by the CCU 51. In the case where the endoscope 20 supports high-resolution shooting such as 4K (3840 horizontal pixels by 2160 vertical pixels) or 8K (7680 horizontal pixels by 4320 vertical pixels) and/or in a case where the endoscope 20 supports 3D display, a display apparatus supporting high-resolution shooting and capable of high-resolution display and/or capable of 3D display can be used, for example, as the display apparatus 53. In the case where the endoscope 20 supports high-resolution shooting such as 4K or 8K, a higher sense of immersion can be acquired by using a display apparatus of 55 inches or larger in size as the display apparatus 53. Also, the plurality of display apparatuses 53 having different resolutions and sizes may be provided in accordance with the purpose of use.

The light source apparatus 55 includes, for example, an LED (light emitting diode) or other light source and supplies irradiation light for shooting an area to be operated on to the endoscope 20.

The arm control apparatus 57 includes, for example, a CPU or other processor and controls the driving of the arm section 43 of the support arm apparatus 40 in accordance with a given control scheme by operating in accordance with a given program.

An input apparatus 59 is an input interface for the endoscopic surgical system 10. A user can input various pieces of information and instructions to the endoscopic surgical system 10 via the input apparatus 59. For example, the user inputs various pieces of information regarding operation such as patient's body information and surgical procedure of operation. Also, for example, the user inputs, via the input apparatus 59, an instruction for driving the arm section 43, an instruction for changing imaging conditions (e.g., irradiation light type, magnification ratio, and focal distance) of the endoscope 20, an instruction for driving the energy treatment tool 33, and so on.

The input apparatus 59 is not limited in type and may be one of various known types of input apparatuses. As the input apparatus 59, for example, a mouse, a keyboard, a touch panel, a switch, a foot switch 69 and/or a lever, and so on can be used. In the case where a touch panel is used as the input apparatus 59, the touch panel may be provided on a display screen of the display apparatus 53.

Alternatively, the input apparatus 59 is, for example, a device worn by the user such as goggle type wearable device or HMD (Head Mounted Display), and various types of inputs are made in response to user's gesture or line of sight detected by these devices. Also, the input apparatus 59 includes a camera capable of detecting user's motion, and various inputs are made in response to user's gesture or line of sight detected from a video captured by the camera.

Further, the input apparatus 59 includes a microphone capable of collecting user's voice, and various inputs can be made by voice via the microphone. As described above, because the input apparatus 59 is configured to permit a variety of information inputs to be made in a non-contact manner, it is possible for the user belonging to a clean region (practitioner 71, for example) to operate equipment belonging to an unclear region. Also, the user can operate the equipment without taking his or her hand off the surgical tool the user is holding, thus ensuring improved ease of use for the user.

A treatment tool control apparatus 61 controls the driving of the energy treatment tool 33 for cauterizing or incising a tissue, sealing a blood vessel, or the like. A pneumoperitoneum apparatus 63 supplies a gas into the body cavity via a pneumoperitoneum tube 31 to inflate the body cavity of the patient 75 so as to secure a field of view of the endoscope 20 and a working space for the practitioner. A recorder 65 is an apparatus capable of recording a variety of types of information regarding operations. A printer 67 is an apparatus capable of printing a variety of types of information regarding operations in various formats such as text, image, and graph.

A further detailed description will be given below, in particular, of characteristic configurations in the endoscopic surgical system 10.
(Support Arm Apparatus)

The support arm apparatus 40 includes the base section 41, a base, and the arm section 43 that extends from the base section 41. Although, in the example illustrated, the arm section 43 includes the plurality of joint sections 45a, 45b, and 45c and the plurality of links 47a and 47b connected by the joint section 45b, the configuration of the arm section 43 is illustrated in a simplified manner for reasons of simplification in FIG. 1.

Actually, not only shapes of the joint sections 45a to 45c and the links 47a and 47b and the number and arrangement thereof but also directions of rotational axes of the joint sections 45a to 45c and so on can be set as appropriate to provide a desired degree of freedom to the arm section 43. For example, the arm section 43 can be suitably configured to offer six degrees of freedom or more. This makes it possible to move the endoscope 20 freely in a motion range of the arm section 43, thus allowing for insertion of the lens barrel 21 of the endoscope 20 into the body cavity of the patient 75 from the desired direction.

The joint sections 45a to 45c have actuators. As a result, the joint sections 45a to 45c are configured to be rotatable around a given rotational axis through driving of the actuators. The driving of the actuators is controlled by the arm control apparatus 57, thus controlling the rotational angle of each of the joint sections 45a to 45c and the driving of the arm section 43. This can realize control over the position and attitude of the endoscope 20. At this time, the arm control apparatus 57 controls the driving of the arm section 43 through various known control schemes such as force control and position control.

For example, the practitioner 71 may make an operation input as appropriate via the input apparatus 59 (including the foot switch 69), so that the driving of the arm section 43 is controlled by the arm control apparatus 57 as appropriate in response to the operation input, and accordingly, the position and attitude of the endoscope 20 are controlled. This control allows for the endoscope 20 at the tip of the arm section 43 to be moved from one arbitrary position to another first and be fixedly supported at the reached position after the movement. It should be noted that the arm section 43 may be operated in a so-called master-slave scheme. In this case, the arm section 43 can be operated remotely by the user via the input apparatus 59 installed at a remote location from an operation room.

Also, in a case where force control is applied, the arm control apparatus 57 may perform so-called power assist control in which an external force is received from the user, and the actuators of the joint sections 45a to 45c are driven such that the arm section 43 moves smoothly to follow the external force. This allows the user to move the arm section 43 with a relatively small force when moving the arm section 43 while directly touching the arm section 43. Therefore, the user can move the endoscope 20 more intuitively and with easier operation, thus ensuring improved ease of use for the user.

Here, it has been common that a medical doctor called a scopist supports the endoscope 20 during endoscopic surgery. In contrast, using the support arm apparatus 40 allows for more secure fixing of the position of the endoscope 20 without human assistance, making it possible to acquire an image of the area to be operated on stably and conduct a surgery smoothly.

It should be noted that the arm control apparatus 57 need not necessarily be provided on the cart 50. Also, the arm control apparatus 57 need not necessarily be a single apparatus. For example, the arm control apparatuses 57 may be provided one for each of the joint sections 45a to 45c of the arm section 43 of the support arm apparatus 40, and control over the driving of the arm section 43 may be realized by coordinated operation of the plurality of arm control apparatuses 57.

(Light Source Apparatus)

The light source apparatus 55 supplies, to the endoscope 20, irradiation light to be used for shooting the area to be operated on. The light source apparatus 55 includes, for example, a white light source that includes an LED or a laser light source or a combination thereof. At this time, in a case where the white light source includes a combination of RGB laser light sources, it is possible to control, with high accuracy, an output intensity and an output timing of each color (each wavelength), thus allowing the light source apparatus 55 to adjust white balance of a captured image.

Also, in this case, images, each corresponding to one of RGB, can be captured in a time-divided manner by irradiating a laser beam from each of the RGB laser light sources in a time-divided manner and controlling the driving of the imaging element of the camera head 23 in synchronism with the irradiation timing thereof. According to the method, a color image can be acquired without providing color filters in the imaging element.

Also, the driving of the light source apparatus 55 may be controlled in such a manner that the intensity of light output therefrom changes every given period of time. It is possible to generate an image with high dynamic range free from so-called blocked up shadows and blown out highlights by controlling the driving of the imaging element of the camera head 23 in synchronism with the moment when the light intensity changes, acquiring images in a time-divided manner, and combining the images.

Also, the light source apparatus 55 may be configured to be capable of supplying light in a given frequency band suitable for special light observation. In special light observation, for example, so-called narrow band imaging is performed in which a given tissue such as blood vessel in a superficial layer of a mucous membrane is shot at high contrast by irradiating light in a narrower band than irradiation light during normal observation (i.e., white light) through exploitation of wavelength dependence of light absorption.

Alternatively, in special light observation, fluorescence observation may be performed in which an image is acquired by means of fluorescence that occurs as a result of irradiation of excitation light. In fluorescence observation, observation of fluorescence from a body tissue after irradiation of excitation light onto the body tissue (autofluorescence observation), acquisition of a fluorescence image by locally injecting a reagent such as India cyanine green (ICG) into a body tissue and irradiating excitation light corresponding to the fluorescence wavelength of the reagent onto the body tissue, and so on are performed. The light source apparatus 55 can be configured to be able to supply narrow-band light and/or excitation light suitable for such special light observation.

(Camera Head and CCU)

Figure 2:
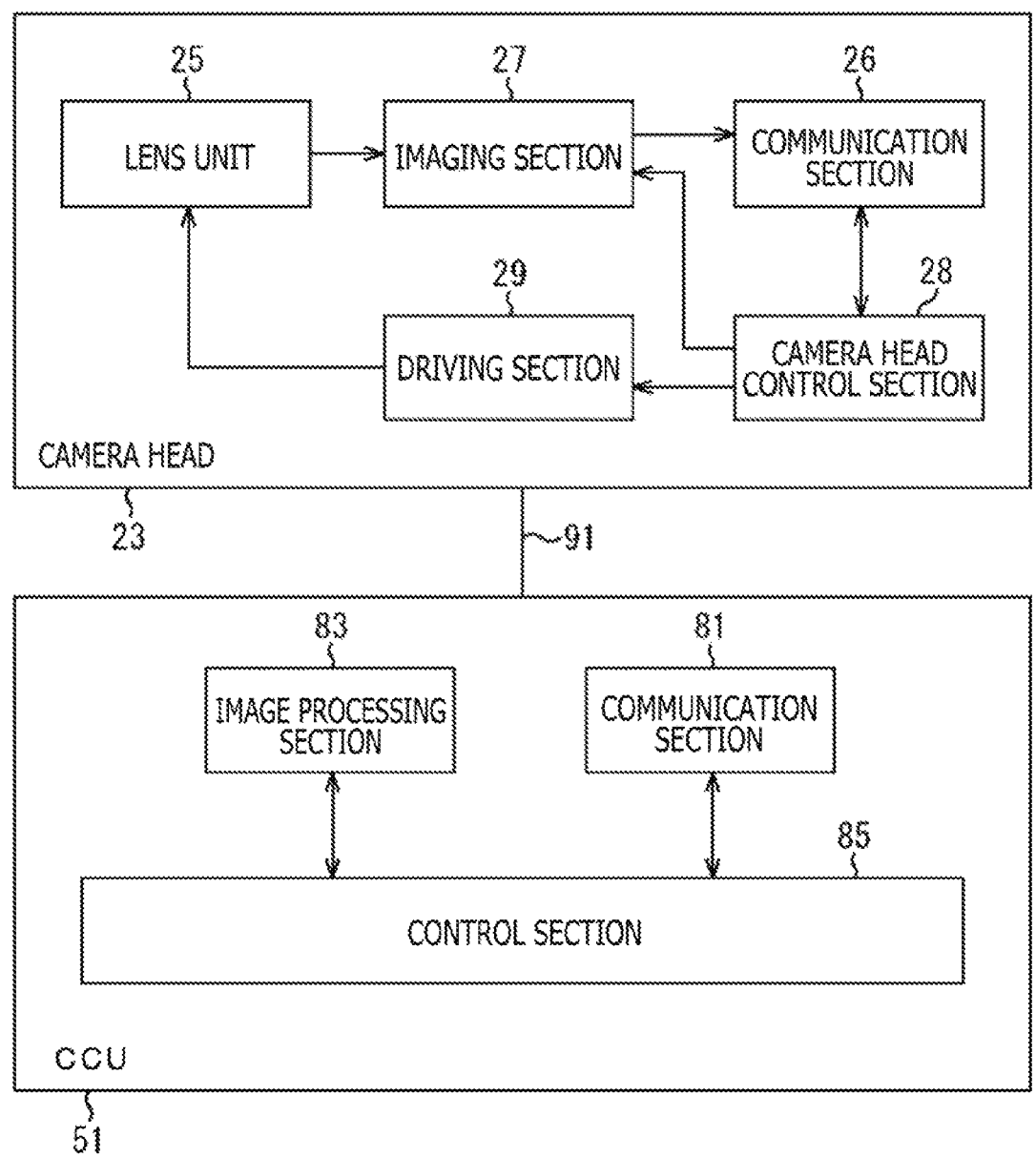
FIG. 2 is a block diagram illustrating an example of functional configuration of a camera head and a CCU.

A more detailed description will be given of functions of the camera head 23 and the CCU 51 of the endoscope 20 with reference to FIG. 2. FIG. 2 is a block diagram illustrating an example of functional configuration of the camera head 23 and the CCU 51 illustrated in FIG. 1.

Referring to FIG. 2, the camera head 23 has, as its functions, a lens unit 25, an imaging section 27, a driving section 29, a communication section 26, and a camera head control section 28. Also, the CCU 51 has, as its functions, a communication section 81, an image processing section 83, and a control section 85. The camera head 23 and the CCU 51 are connected by a transmission cable 91 to allow bidirectional communication.

A description will be given first of a functional configuration of the camera head 23. The lens unit 25 is an optics provided in a connection section with the lens barrel 21. Observation light taken in from the tip of the lens barrel 21 is guided to the camera head 23 and enters the lens unit 25. The lens unit 25 includes a combination of a plurality of lenses including a zoom lens and a focusing lens. Optical characteristics of the lens unit 25 have been adjusted in such a manner as to converge observation light a light-receiving surface of the imaging element of the imaging section 27. Also, the zoom lens and the focusing lens are configured to be able to move their positions on an optical axis thereof for adjustment of a magnification ratio and a focal point of a captured image.

The imaging section 27 includes an imaging element and is arranged at a subsequent stage of the lens unit 25.

Observation light that has passed through the lens unit 25 is converged on the light-receiving surface of the imaging element, generating an image signal proportional to an observation image through photoelectric conversion. The image signal generated by the imaging section 27 is supplied to the communication section 26.

For example, a CMOS (Complementary Metal Oxide Semiconductor)-type image sensor having a Bayer pattern and capable of color shooting is used as an imaging element included in the imaging section 27. It should be noted that an image sensor supporting, for example, 4K or higher high-resolution image shooting may be used. The acquisition of a high-resolution image of the area to be operated on allows the practitioner 71 to grasp the appearance of the area to be operated on in more detail for smooth progress of the surgery.

Also, the imaging element included in the imaging section 27 is configured to have a pair of imaging elements, one for acquiring a right eye image signal and another for acquiring a left eye image signal, both for 3D display. The practitioner 71 can more accurately grasp a depth of the body tissue in the area to be operated on thanks to 3D display. It should be noted that in a case where the imaging section 27 includes multiple image elements, the plurality of lens units 25 are provided to correspond to the respective imaging elements.

Also, the imaging section 27 need not necessarily be provided in the camera head 23. For example, the imaging section 27 may be provided immediately after the objective lens in the lens barrel 21.

The driving section 29 includes an actuator and moves, under control of the camera head control section 28, the zoom lens and the focusing lens of the lens unit 25 by a given distance along the optical axis. This allows for adjustment of the magnification ratio and the focal point of the image captured by the imaging section 27 as appropriate.

The communication section 26 includes a communication apparatus for exchanging various types of information with the CCU 51. The communication section 26 sends an image signal, acquired from the imaging section 27 to the CCU 51 via the transmission cable 91 as RAW data. At this time, it is preferable that the image signal be sent through optical communication to display a captured image of the area being operated on with low latency.

During surgery, the practitioner 71 performs the surgery while observing the patient's condition with a captured image. In order to ensure higher safety and reliability in surgery, therefore, a video of the area being operated on is required to be displayed in real time to the extent possible. In the case where the image is sent through optical communication, a photoelectric conversion module for converting an electric signal into an optical signal is provided in the communication section 26. The image signal is converted into an optical signal first by the photoelectric conversion module, followed by transmission of the optical signal to the CCU 51 via the transmission cable 91.

Also, the communication section 26 receives, from the CCU 51, a control signal for controlling the driving of the camera head 23. The control signal includes, for example, information regarding imaging conditions such as information specifying a frame rate of the captured image, information specifying an exposure value during imaging, and/or information specifying a magnification ratio and a focal point of the captured image. The communication section 26 supplies the received control signal to the camera head control section 28.

It should be noted that a control signal from the CCU 51 may be transmitted through optical communication. In this case, a photoelectric conversion module for converting an optical signal into an electric signal is provided in the communication section 26. The control signal is converted into an electric signal first by the photoelectric conversion module and then supplied to the camera head control section 28.

It should be noted that the imaging conditions described above such as frame rate, exposure value, magnification ratio, and focal point are automatically set by the control section 85 of the CCU 51 on the basis of the image signal acquired. That is, the endoscope 20 incorporates so-called AE (Auto Exposure), AF (Auto Focus), and AWB (Auto White Balance) functions.

The camera head control section 28 controls the driving of the camera head 23 on the basis of the control signal received from the CCU 51 via the communication section 26. For example, the camera head control section 28 controls the driving of the imaging element of the imaging section 27 on the basis of information specifying the frame rate of the captured image and/or information specifying the exposure during imaging. Also, for example, the camera head control section 28 moves, as appropriate, the zoom lens and the focusing lens of the lens unit 25 via the driving section 29 on the basis of information specifying the magnification ratio and the focal point of the captured image. The camera head control section 28 may further incorporate a function to store information for identifying the lens barrel 21 and the camera head 23.

It should be noted that the camera head 23 offers can be rendered resistant to an autoclave sterilization process by arranging the components such as the lens unit 25 and the imaging section 27 in a highly airtight and waterproof sealed structure.

A description will be given next of the functional configuration of the CCU 51. The communication section 81 includes a communication apparatus for exchanging various types of information with the camera head 23. The communication section 81 receives an image signal sent from the camera head 23 via the transmission cable 91. At this time, the image signal can be suitably sent through optical communication as described above. In this case, a photoelectric conversion module for converting an optical signal into an electric signal is provided in the communication section 81 to support optical communication. The communication section 81 supplies the image signal that has been converted into an electric signal to the image processing section 83.

Also, the communication section 81 sends a control signal to the camera head 23 to control the driving thereof. The control signal may be also sent through optical communication.

The image processing section 83 performs a variety of image processing procedures on the image signal, RAW data sent from the camera head 23. The image processing procedures include various known signal processing procedures such as development process, image quality improvement processes (e.g., bandwidth enhancement, super-resolution, and NR (Noise reduction), and/or hand shake correction process), and/or enlargement process (electronic zooming process). Also, the image processing section 83 performs an image signal detection process for AE, AF, and AWB.

The image processing section 83 includes a processor such as CPU or GPU, and the processor operates in accordance with a given program, thus allowing the above imaging processing procedures and the detection process to be performed. It should be noted that in a case where the image processing section 83 includes a plurality of GPUs, the image processing section 83 divides information relating to an image signal as appropriate to perform image processing in parallel with the plurality of GPUs.

The control section 85 performs various types of control relating to imaging of the area operated on with the endoscope 20 and display of the captured image. For example, the control section 85 generates a control signal for controlling the driving of the camera head 23. At this time, in a case where the imaging conditions have been input by the user, the control section 85 generates a control signal on the basis of the user inputs. Alternatively, in a case where the endoscope 20 incorporates AE, AF, and AWB functions, the control section 85 generates a control signal by calculating the optimal exposure value, focal distance, and white balance in accordance with the detection results of the image processing section 83.

Also, the control section 85 causes an image of the area operated on to be displayed on the display apparatus 53 on the basis of the image signal subjected to image processing by the image processing section 83. At this time, the control section 85 recognizes various objects in the image of the area operated on by using various image recognition technologies.

For example, the control section 85 can recognize surgical tools such as forceps, specific biological part, bleeding, and mist during use of the energy treatment tool 33 by detecting shapes, colors, and other features of edges of objects included in the image of the area operated on. When causing an image of the area operated on to be displayed on the display apparatus 53, the control section 85 causes various pieces of surgery support information to be superimposed on the image of the area operated on by using the recognition results. Superimposition of surgery support information and presentation of the information to the practitioner 71 ensures safety and reliability in surgery.

The transmission cable 91 connecting the camera head 23 and the CCU 51 is an electric signal cable that supports electric signal communication, an optical fiber that supports optical communication, or a composite cable thereof.

Here, although, in the example illustrated, wired communication is carried out using the transmission cable 91, communication between the camera head 23 and the CCU 51 may be achieved in a wireless manner. In the case where the two communicate in a wireless manner, there is no need to lay the transmission cable 91 in the operation room, possibly eliminating interference in the movement of medical staff by the transmission cable 91 in the operation room.

A description has been given above of an example of the endoscopic surgical system 10 to which the technology according to the present disclosure is applicable.

It should be noted that the endoscopic surgical system 10 has been described here as an example, systems to which the technology according to the present disclosure is applicable are not limited to the example. For example, the technology according to the present disclosure may be applied to a flexible endoscopic inspection system and a microsurgical system.

In the description given below, a description will be continued by taking the endoscopic surgical system 10 described above as an example to which the present technology is applied. In the endoscopic surgical system 10 to which the present technology is applied, a normal image and a special image are acquired, and the acquired normal and special images can be presented superimposed one on the other to the practitioner.

Figure 3:
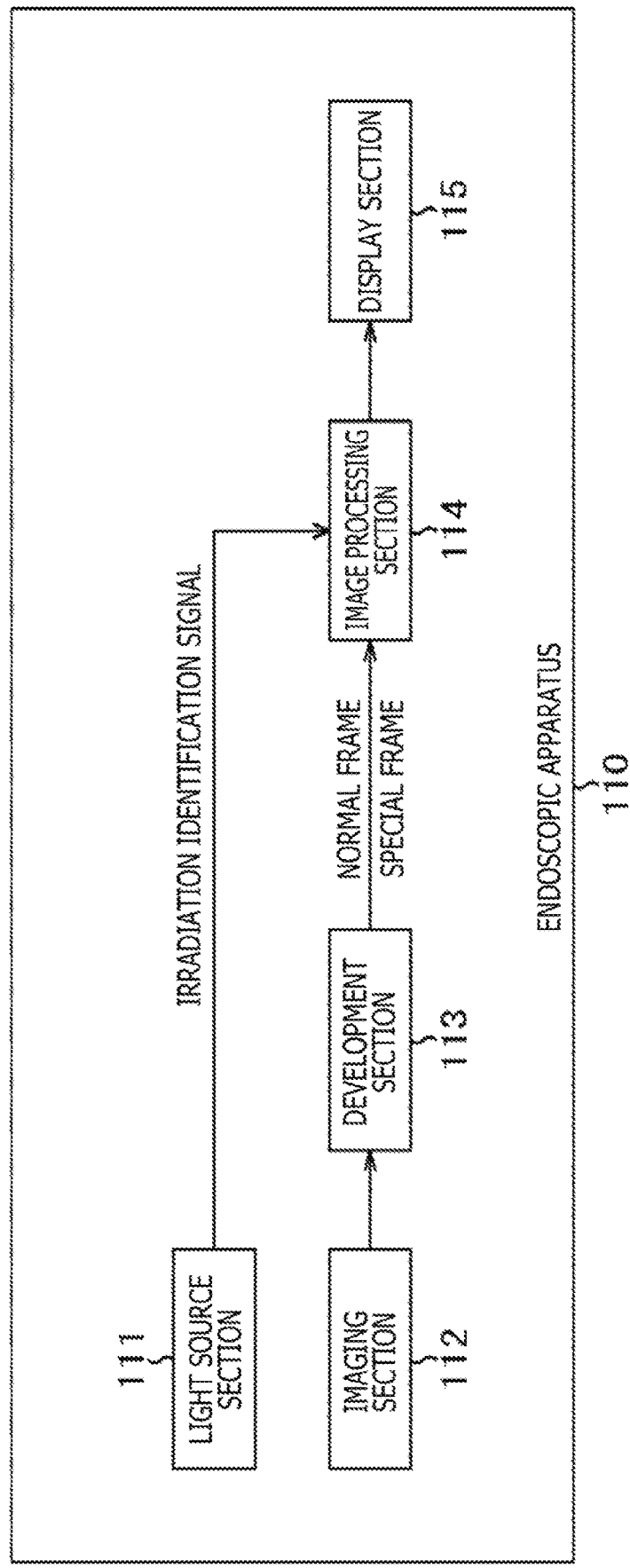
FIG. 3 is a block diagram illustrating a configuration example of an endoscopic apparatus.

In order to additionally describe the acquisition of normal and special images and the superimposition of the acquired normal and special images, the configuration of the endoscopic surgical system will be described again. FIG. 3 is a diagram illustrating a configuration example of an endoscopic apparatus having functions of acquiring normal and special images, superimposing the acquired normal and special images, and presenting a superimposed image.

Here, a normal image refers to an image captured with normal light irradiated, for example, on an organ, a subject. A normal image will be hereinafter also referred to as a normal frame. A special image refers to an image captured with special light having a given wavelength different from that of the normal light irradiated. A special image will be hereinafter also referred to as a special frame. It should be noted that when a special image is captured, a fluorescence agent that reacts to irradiated special light is mixed or applied to blood vessels (blood) or lesions, a subject.

An endoscopic apparatus 110 illustrated in FIG. 3 depicts a configuration example of an endoscopic apparatus that captures normal and special frames in a time-divided manner, combines these images through accurate alignment, and displays a combined frame acquired as a result thereof.

The endoscopic apparatus 110 includes a light source section 111, an imaging section 112, a development section 113, an image processing section 114, and a display section 115. The light source section 111 corresponds, for example, to the light source apparatus 55 (FIG. 1) of the endoscopic surgical system 10, and the imaging section 112 corresponds to the imaging section 27 (FIG. 2). The development section 113 is included in the image processing section 83 (FIG. 2), and the image processing section 114 corresponds to the image processing section 83 (FIG. 2), and the display section 115 corresponds to the display apparatus 53 (FIG. 1).

The light source section 111 switches, for each frame captured, between normal light such as white light and special light having a given wavelength for irradiation onto the subject (e.g., organ inside the body). Also, the light source section 111 outputs to the image processing section 114, for each frame captured, an irradiation identification signal indicating which light, normal light or special light, has been irradiated. It should be noted that, in order to irradiate special light, it is sufficient if an optical filter that passes only given wavelengths is provided in an optical path of normal light.

The imaging section 112 captures an image of a subject irradiated with normal light or special light from the light source section 111 and outputs an image signal acquired as a result thereof to the development section 113. The development section 113 performs a development process such as mosaicing process on the image signal input from the imaging section 112 and outputs the image signal resulting therefrom (normal frame at the time of irradiation of normal light or special frame at the time of irradiation of special light) to the image processing section 114.

Here, the special frame provides a clearer view of blood vessels and lesions such as tumors than the normal frame. On the other hand, the frame is dark as a whole and has much noise. In the meantime, the normal frame is brighter as a whole than the special frame and has little noise. On the other hand, it is difficult to find blood vessels and lesions such as tumors.

The image processing section 114 detects a motion vector by using two normal frames having different capture timings. Also, the image processing section 114 performs motion correction of a special frame on the basis of the motion vector detected from the normal frames, combines the normal frame and the special frame subjected to motion correction, and outputs a combined frame acquired as a result thereof to the display section 115.

The display section 115 displays the combined frame.

<Capture Timings of Normal and Special Frames>

Figure 4:
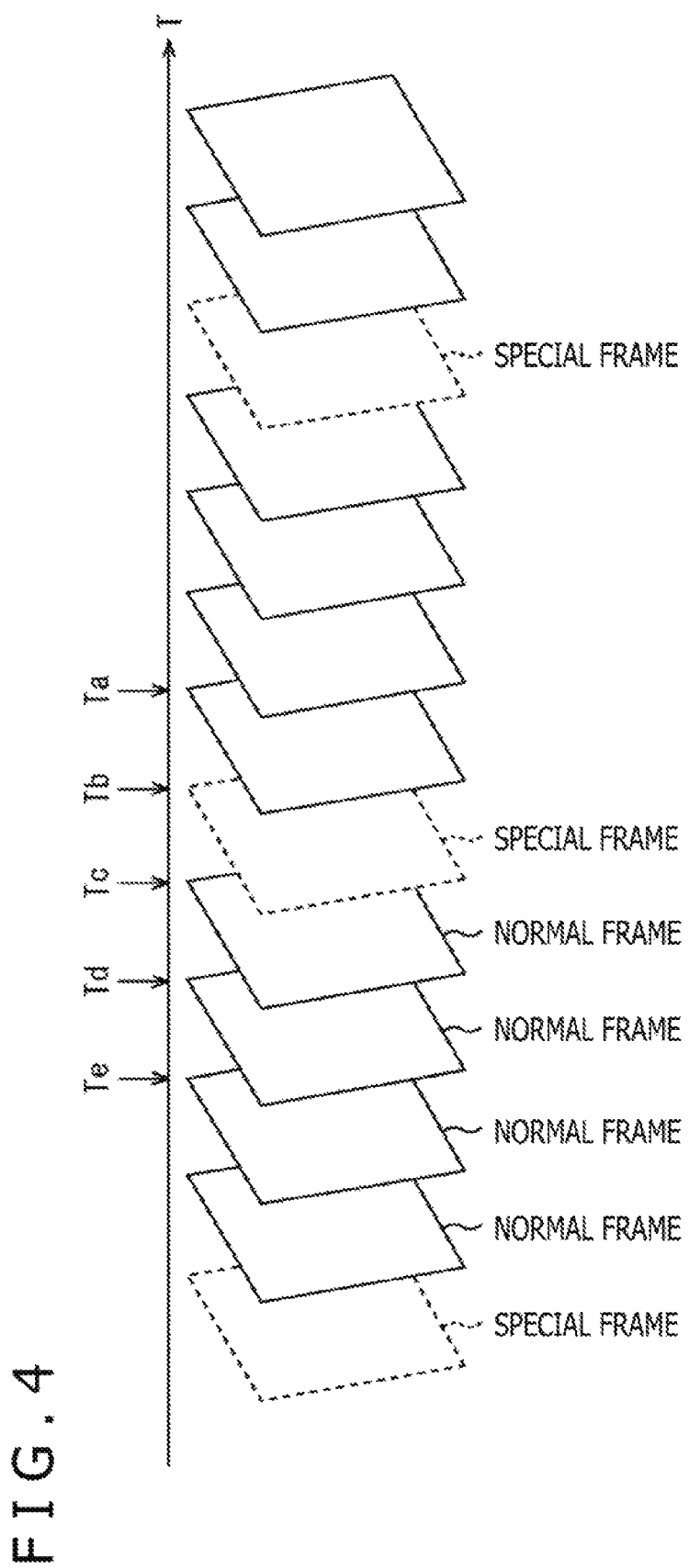
FIG. 4 is a diagram illustrating capture timings of a normal frame and a special frame.

FIG. 4 is a diagram illustrating examples of capture timings of a normal frame and a special frame.

In the endoscopic apparatus 110, several normal frames are captured in series, and during that time period, special frames are captured by definition. For example, normal and special frames are captured at a 4:1 ratio as illustrated in FIG. 4.

It should be noted, however, that this ratio is not limited to 4:1 and may be variable. Reference numeral Ta in FIG. 4 represents the timing when a normal frame is captured one frame previous to the capture of a special frame, reference numeral Tb represents the timing when a special frame is captured, and reference numerals Tc, Td, and Te represent the timings when normal frames are captured, respectively, one, two, and three frames after the capture of the special frame. Reference numerals Ta to Te will be used for description of motion vector detection which will be described later.

<Configuration Example of Image Processing Section 114>

Figure 5:
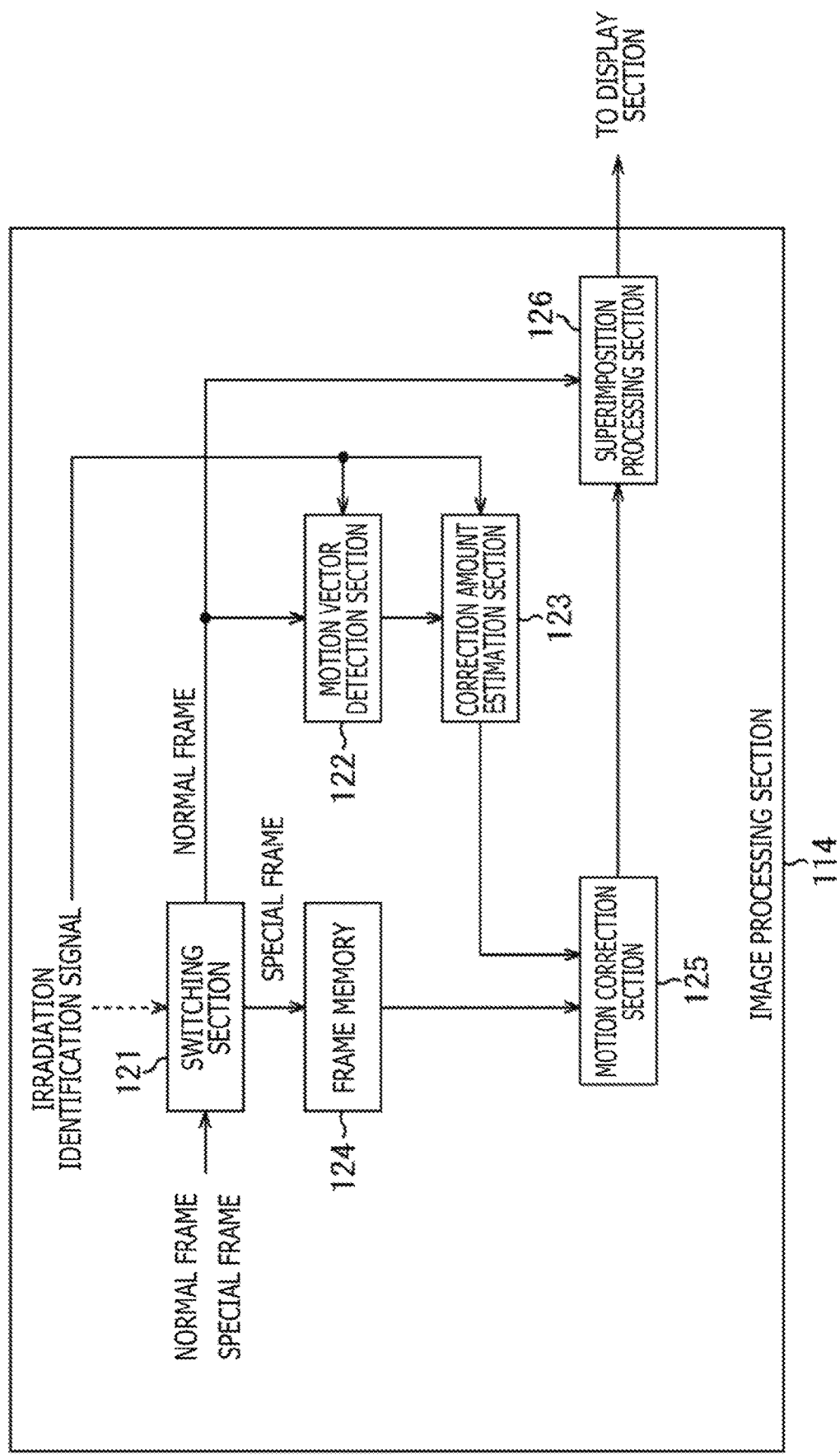
FIG. 5 is a block diagram illustrating a detailed configuration example of an image processing section.

Next, FIG. 5 illustrates a configuration example of the image processing section 114.

The image processing section 114 includes a switching section 121, a motion vector detection section 122, a correction amount estimation section 123, a frame memory 124, a motion correction section 125, and a superimposition processing section 126.

In the image processing section 114, normal and special frames input from the development section 113 at the previous stage are input to the switching section 121, and an irradiation identification signal from the light source section 111 is input to the switching section 121, the motion vector detection section 122, and the correction amount estimation section 123.

The switching section 121 determines, on the basis of the irradiation identification signal, whether or not the input from the development section 113 is a special frame. In the case where the input is not a special frame (is a normal frame), the switching section 121 outputs the frame to the motion vector detection section 122 and the superimposition processing section 126. In the case where the input is a special frame, the switching section 121 outputs the frame to the frame memory 124.

The motion vector detection section 122 detects, during every frame period, a motion vector by using two normal frames having different capture timings and outputs the detected motion vector to the correction amount estimation section 123.

The correction amount estimation section 123 estimates, on the basis of the motion vector detected by the motion vector detection section 122, a motion correction amount of the special frame and outputs the estimated motion correction amount to the motion correction section 125. It should be noted that the correction amount estimation section 123 can correct, on the basis of motion vectors that have been detected in series, a motion vector that may have been erroneously detected, and estimate a motion correction amount on the basis of the corrected motion vector.

The frame memory 124 holds a special frame input from the switching section 121 and supplies the held frame to the motion correction section 125 during every frame period. Also, in a case where a next special frame is input from the switching section 121, the frame memory 124 updates the held frame.

It should be noted that, for example, a process may be performed to extract a region with (3×3) variance or dynamic range equal to or higher than a threshold inside a microblock and generate a feature extraction frame representing the extraction result. Also, for example, a process may be performed to extract a region with a specific pixel signal level, i.e., a region with a specific RGB level and generate a feature extraction frame representing the extraction result. Also, for example, a contour detection process such as SNAKE may be performed on a closed region (corresponding, for example, to a tumor) so as to generate a feature extraction frame representing the result thereof.

The motion correction section 125 corrects the motion of the special frame from the frame memory 124 on the basis of the motion correction amount input from the correction amount estimation section 123 and outputs the special frame subjected to the motion correction to the superimposition processing section 126.

The superimposition processing section 126 receives, as inputs, a normal frame and a special frame subjected to motion correction, generates a combined frame (superimposed frame) through a superimposition/combining process, and outputs the combined frame to the display section 115 at the subsequent stage.

<Configuration Example of Motion Vector Detection Section 122>

Figure 6:
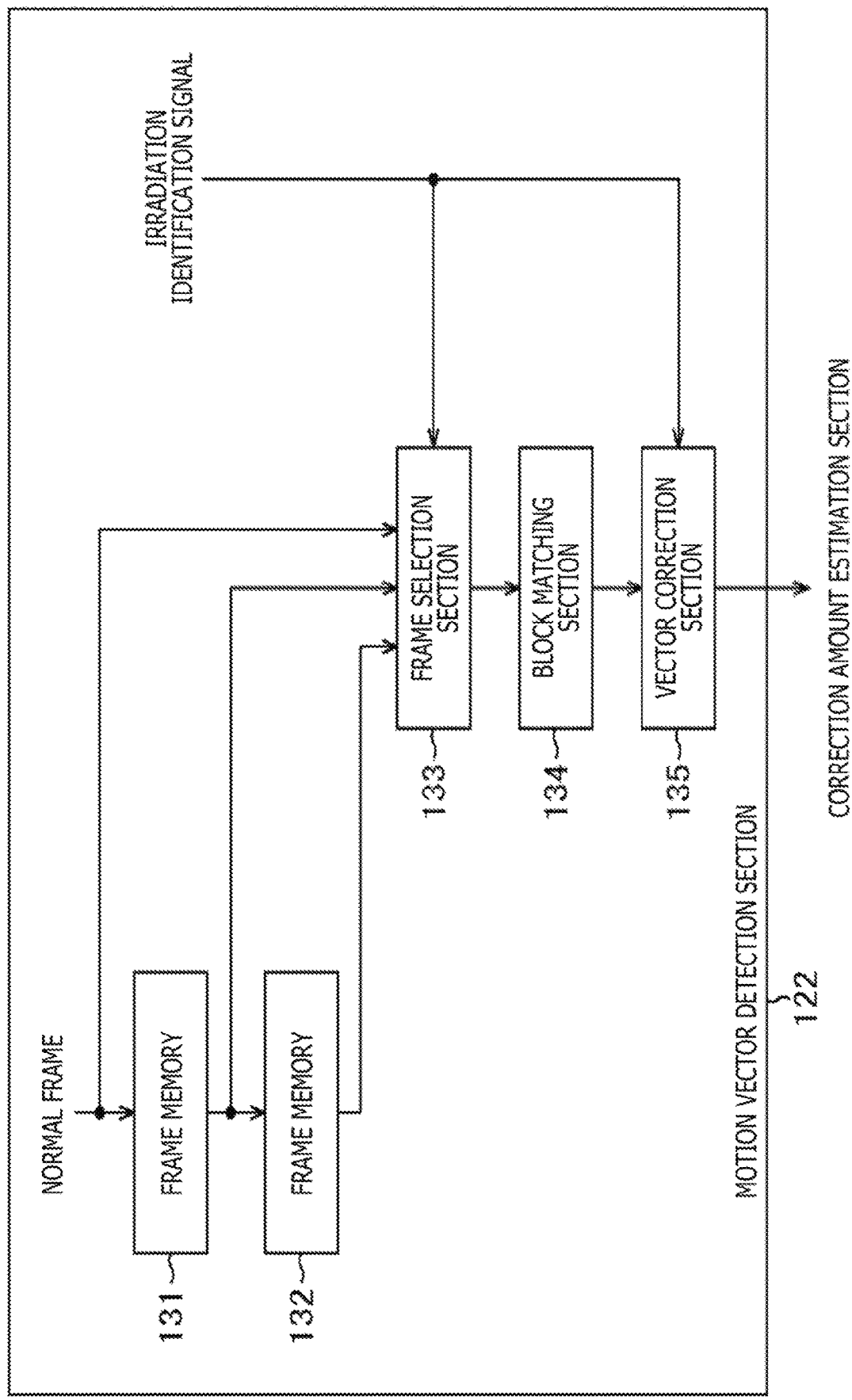
FIG. 6 is a block diagram illustrating a detailed configuration example of a motion vector detection section.

FIG. 6 illustrates a configuration example of the motion vector detection section 122. The motion vector detection section 122 includes frame memories 131 and 132, a frame selection section 133, a block matching section 134, and a vector correction section 135.

In the motion vector detection section 122, the normal frame input from the switching section 121 at the previous stage is input to the frame memory 131 and the frame selection section 133.

The frame memory 131 outputs, during every frame period, the normal frame held up to that moment to the frame memory 132 and the frame selection section 133 and updates the held data with a normal frame input from the switching section 121. Similarly, the frame memory 132 outputs, during every frame period, the held normal frame to the frame selection section 133 and updates the held data with a normal frame input from the frame memory 131 at the previous stage.

It should be noted that, at a timing during a frame period when a normal frame is not input to the motion vector detection section 122, the frame memory 131 outputs the normal frame held up to that moment to the subsequent stage and clears itself of the data.

At the next timing, the frame memory 131 does not hold any data and, therefore, does not output any data to the subsequent stage. The frame memory 132 outputs the normal frame held up to that moment to the subsequent stage and clears itself of the data.

Therefore, two or three normal frames having different capture timings are input to the frame selection section 133 at the same time.

In the case where two normal frames are input at the same time, the frame selection section 133 outputs the two normal frames to the block matching section 134. Also, in a case where three normal frames are input at the same time, the frame selection section 133 outputs the two normal frames input from the frame memories 131 and 132 to the block matching section 134. The block matching section 134 detects a motion vector between the two normal frames through a block matching process.

The vector correction section 135 determines a relationship between the two normal frames used for the motion vector on the basis of an irradiation identification signal, corrects the detected motion vector on the basis of the relationship, and outputs the motion vector to the correction amount estimation section 123.

A specific description will be given of correction of a motion vector by the vector correction section 135. Assuming output from the frame memory 131 as a reference, in a case where a reference capture timing is Ta illustrated in FIG. 4, a normal frame one frame previous to a reference frame and a reference normal frame are input to the frame selection section 133 respectively from the frame memory 132 and the frame memory 131, and motion vectors are detected from these two normal frames. In this case, the vector correction section 135 does not correct the motion vectors.

In the case where the reference capture timing is Tb illustrated in FIG. 4, Tb is a capture timing of a special frame. Therefore, the frame memory 131 does not output any data. Then, a normal frame one frame previous to the reference frame and a normal frame one frame subsequent to the reference frame are input to the frame selection section 133 respectively from the frame memory 131 and the switching section 121, and motion vectors are detected from these two normal frames. In this case, the detected motion vector is a vector between the normal frames that are two frames apart. Therefore, the vector correction section 135 multiplies respective vertical and horizontal components of the detected motion vectors by ½.

In the case where the reference capture timing is Tc illustrated in FIG. 4, a reference normal frame and a normal frame one frame subsequent to a reference frame are input to the frame selection section 133 respectively from the frame memory 131 and the switching section 121, and motion vectors are detected from these two normal frames. In this case, the detected motion vectors are opposite in direction. Therefore, the vector correction section 135 multiplies the respective vertical and horizontal components of the detected motion vectors by −1.

In the case where the reference capture timing is Td illustrated in FIG. 4, a normal frame one frame previous to a reference frame, a reference normal frame, and a normal frame one frame subsequent to a reference frame are input to the frame selection section 133 respectively from the frame memory 132, the frame memory 131, and the switching section 121, and motion vectors are detected from the two normal frames from the frame memories 131 and 132. In this case, the vector correction section 135 does not correct the motion vectors.

In the case where the reference capture timing is Te illustrated in FIG. 4, a normal frame one frame previous to a reference frame, a reference normal frame, and a normal frame one frame subsequent to a reference frame are input to the frame selection section 133 respectively from the frame memory 132, the frame memory 131, and the switching section 121, and motion vectors are detected from the two normal frames from the frame memories 131 and 132. In this case, the vector correction section 135 does not correct the motion vectors.

The motion vector corrected as described above is output to the correction amount estimation section 123 in the subsequent stage from the vector correction section 135.

<Image Combining Process by Image Processing Section 114>

Figure 7:
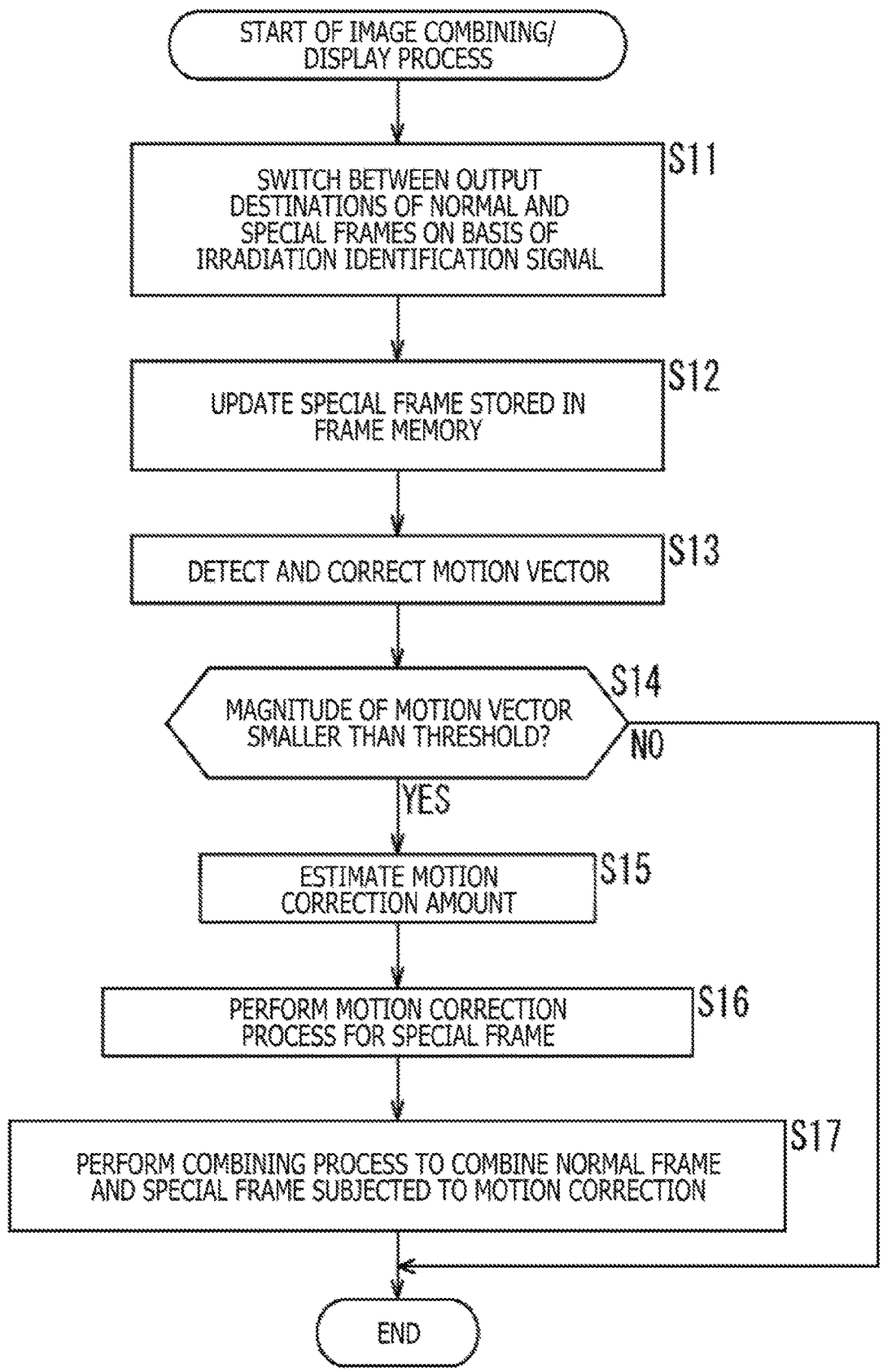
FIG. 7 is a flowchart describing an image combining process.

A description will be given next of an image combining process by the image processing section 114 with reference to FIG. 7. FIG. 7 is a flowchart describing the image combining process. This image combining process is performed every frame period.

In step S11, the switching section 121 determines, on the basis of an irradiation identification signal, whether or not the input from the development section 113 is a special frame. In the case where it is determined that the input is a special frame, the switching section 121 outputs the special frame to the frame memory 124. Conversely, in a case where it is determined that the input is not a special frame (is a normal frame), the switching section 121 outputs the frame to the motion vector detection section 122 and the superimposition processing section 126.

In step S12, the frame memory 124 supplies the special frame held up to that moment to the motion correction section 125. It should be noted that in a case where a special frame is input from the switching section 121, the frame memory 124 updates the held special frame.

In step S13, the motion vector detection section 122 detects a motion vector by using two normal frames having different capture timings and outputs the motion vector to the correction amount estimation section 123. In step S14, the correction amount estimation section 3 determines whether or not the detected motion vector is equal to or lower than a given threshold, and in a case where the detected motion vector is equal to or lower than the given threshold, the process proceeds to step S15 to use the motion vector for motion correction. Conversely, in a case where the detected motion vector is greater than the given threshold, the motion vector is not used for motion correction. In this case, the image combining process corresponding to the current capture timing is terminated.

In step S15, the correction amount estimation section 123 estimates a motion correction amount of the special frame on the basis of the motion vector detected by the motion vector detection section 122 and outputs the estimated motion correction amount to the motion correction section 126.

After the estimation of the motion correction amount, the process proceeds to step S16. In step S16, the motion correction section 125 corrects the motion of the special frame from the frame memory 124 on the basis of the motion correction amount input from the correction amount estimation section 123 and outputs the special frame subjected to the motion correction to the superimposition processing section 126. The normal frame and the special frame input to the superimposition processing section 126 have their respective subjects accurately aligned.

In step S17, the superimposition processing section 126 generates a combined frame by performing a superimposition/combining process using the normal frame and the special frame subjected to the motion correction and outputs the combined frame to the display section 115 at the subsequent stage.

Thanks to the processes described above, the endoscopic apparatus 110 can detect a motion vector using only normal frames and estimate a motion correction amount after correcting the detected motion vector, thus allowing for accurate motion correction of a special frame. As a result, it is possible to accurately align special frame information such as blood vessels and tumors in the normal frame, thus allowing for the user (e.g., medical doctor performing operation) to accurately and clearly visually identify the tumor area to be excised and the blood vessel area not to be excised.

Created on the basis of a normal frame, a combined frame that is brighter and has less noise than a special frame can be presented to the user.

<Signal Level of Superimposed Portion>

As described above, in a case where a combined frame is generated by simply adding pixel values in superimposing normal and special frames, there is a region where a signal becomes saturated, in other words, there is a region where a signal exceeds a maximum value that can be taken on by a digital signal value. As a result, there is a possibility that a poorly visible image deprived, in particular, of detailed information included in the special image may be produced.

Figure 8:
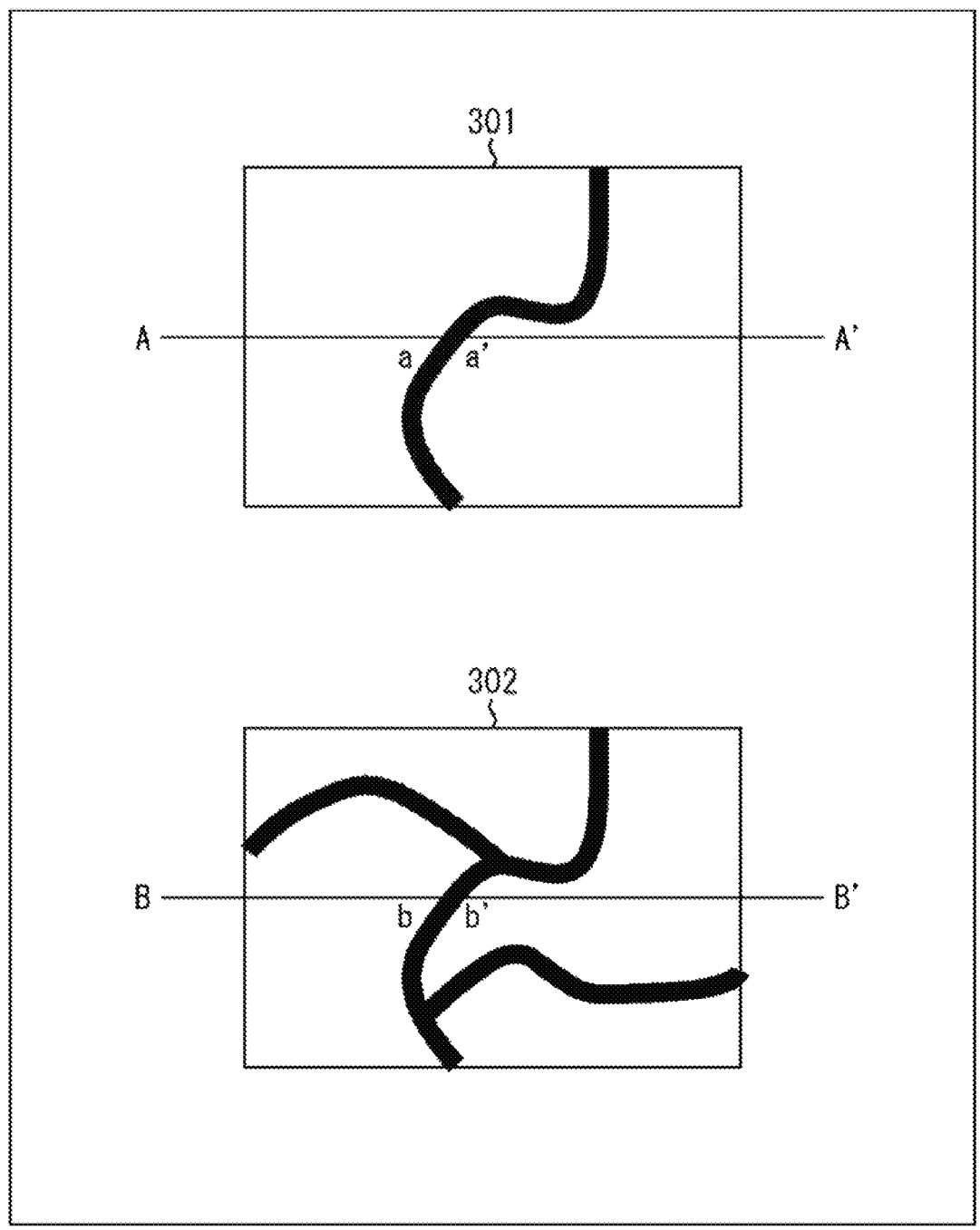
FIG. 8 depict diagrams illustrating examples of captured frames.

Consider, for example, a case in which a normal frame 301 and a special frame 302 as illustrated in FIG. 8 are acquired. The normal frame 301 includes a visually identifiable blood vessel captured therein. The special frame 302 includes, in addition to a visually identifiable result, a blood vessel not captured in the normal frame 301 captured therein.

Figure 9:
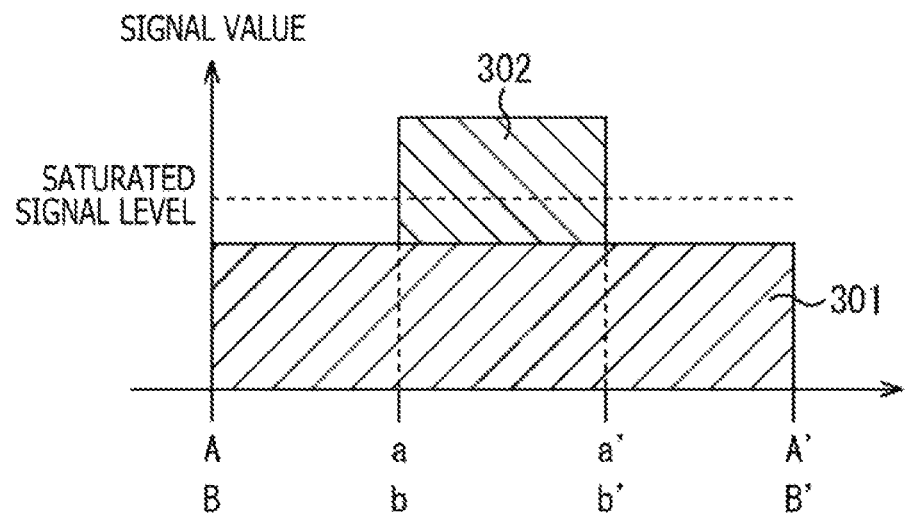
FIG. 9 is a diagram for describing a signal level after combining.

Consider a case in which the normal frame 301 and the special frame as described above are superimposed. Consider the superimposition of a line A-A' of the normal frame 301 and a line B-B' of the special frame located at a position corresponding to the line A-A'. In this case, having the position along the horizontal axis and the signal level along the vertical axis, a graph as illustrated in FIG. 9 is acquired.

Of the line A-A' in the normal frame 301, a blood vessel is captured in a portion a-a'. Similarly, of the line B-B' in the special frame 302, a blood vessel is captured in a portion b-b'. The signal level of none of the pixels on the line A-A' in the normal frame 301 exceeds a saturation level.

In the case where the special frame 302 is superimposed on the normal frame 301, of the line B-B' in the special frame 302, the blood vessel in the portion b-b' is superimposed on the blood vessel in the portion a-a' of the line A-A' in the normal frame 301.

The superimposition of the blood vessel in the portion a-a' and the blood vessel in the portion b-b' leads to a possibility that the saturation signal level may be exceeded. If the saturation signal level is exceeded, blown out highlights, for example, may occur, resulting in loss of detailed information. For example, if the superimposition leads to a signal level beyond the saturation signal level despite the fact that a plurality of blood vessels are captured, there is a possibility that an image may be displayed in such a manner that the plurality of blood vessels are unidentifiable, resulting in loss of detailed information.

In the case where normal and special frames are superimposed, for example, at a given mixing ratio that ensures that the signal level remains under the saturation signal level after the superimposition in order to achieve superimposition of the normal and special frames with the signal level maintained under the saturation signal level, there is a possibility that peripheral information (e.g., information regarding a periphery of an affected site) may become dark, possibly resulting in an image deprived of detailed peripheral information.

Consider, for example, a case in which the normal frame 301 and the special frame 302 as illustrated in FIG. 8 are acquired similarly as described above. The superimposition of the blood vessel in the portion a-a' and the blood vessel in the portion b-b' leads to a possibility that the saturation signal level may be exceeded. Therefore, the signal level of the normal frame is reduced in advance.

Figure 10:
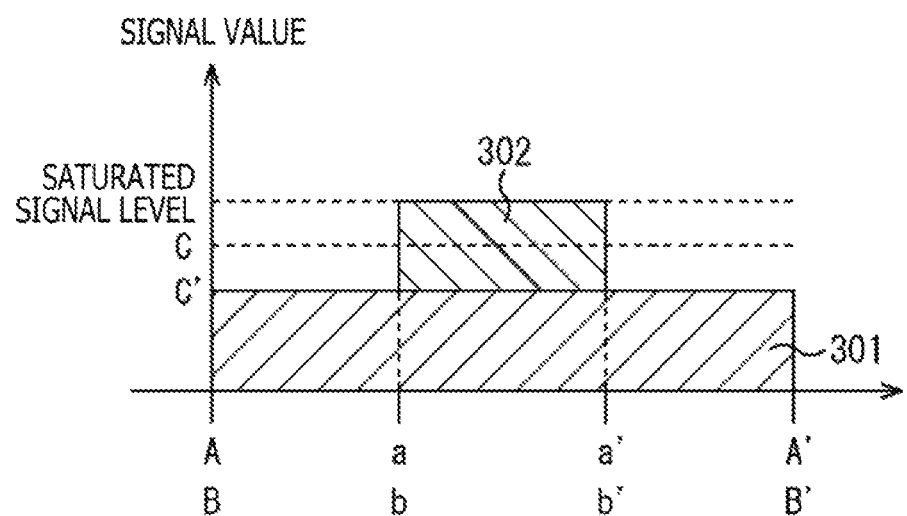
FIG. 10 is a diagram for describing a signal level after combining.

For example, although the signal level of the acquired normal frame 301 is a level C as illustrated in FIG. 10, the signal level is converted from the level C to a level C' which is lower than the level C, and then the normal frame 301 is superimposed with the special frame 302.

The superimposition after reduction of the signal level as described above ensures that the saturation signal level is not exceeded even if the blood vessel in the portion a-a' and the blood vessel in the portion b-b' are superimposed.

However, although supposed to be at the level C, the signal level of the normal frame 301 has been reduced to the level C'. This leads, for example, to a possibility that the image in the normal frame 301 may become dark and more difficult to see due to reduced brightness.

It is possible, by applying the present technology described below, to superimpose normal and special frames without losing detailed information.

<Configuration of Superimposition Processing Section>

Figure 11:
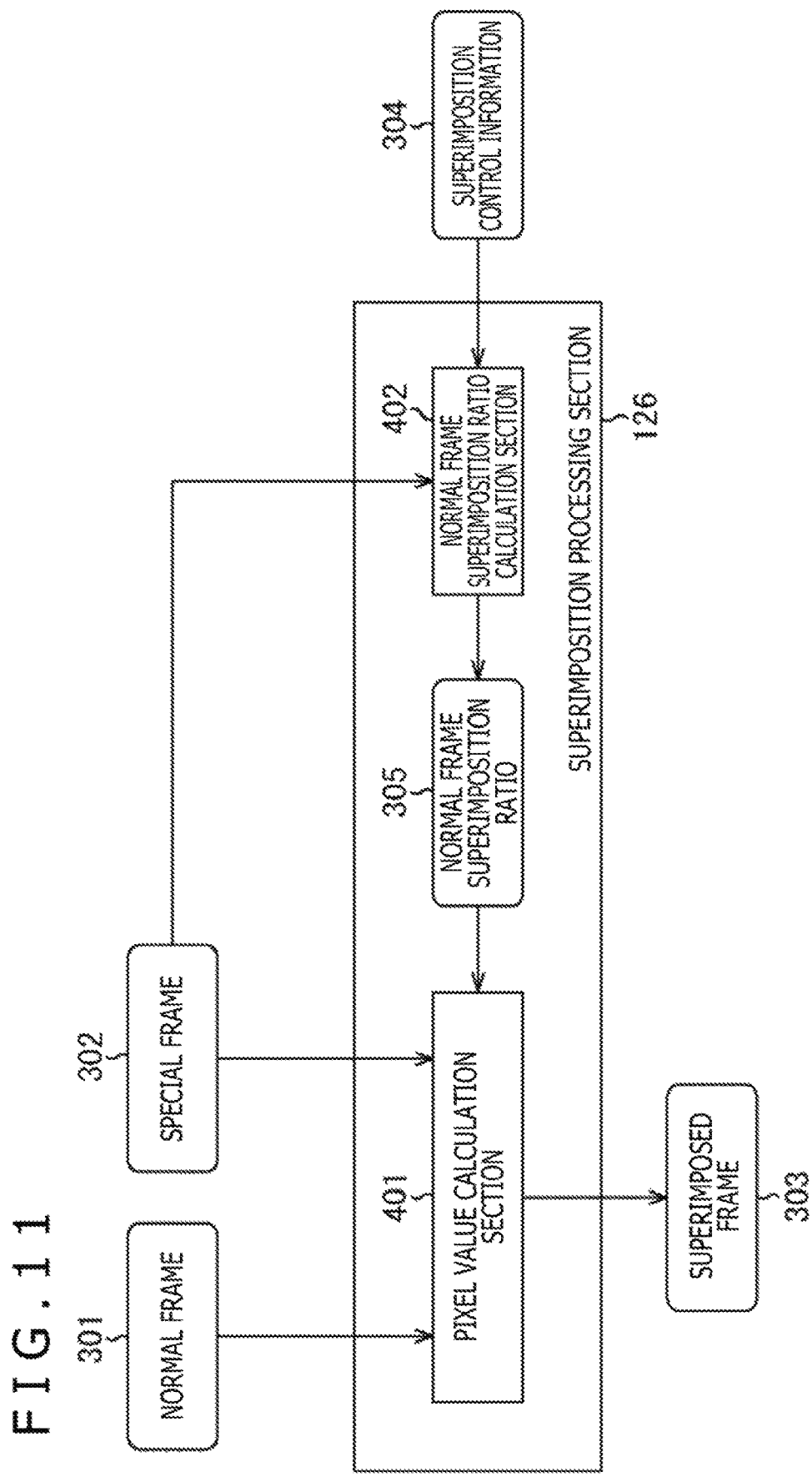
FIG. 11 is a diagram for describing a configuration of a superimposition processing section.

FIG. 11 is a diagram illustrating an internal configuration example of the superimposition processing section 126. The superimposition processing section 126 includes a pixel value calculation section 401 and a normal frame superimposition ratio calculation section 402.

The special frame 302 is supplied to the normal frame superimposition ratio calculation section 402 of the superimposition processing section 126. The normal frame superimposition ratio calculation section 402 calculates a mixing ratio between the normal frame 301 and the special frame 302 for superimposing the normal frame 301 and the special frame 302, for example, with reference to a brightness value of the supplied special frame 302.

Superimposition control information 304 is also supplied to the normal frame superimposition ratio calculation section 402. The normal frame superimposition ratio calculation section 402 calculates a mixing ratio on the basis of the superimposition control information 304. Here, a description will be continued assuming that the normal frame superimposition ratio calculation section 402 calculates a normal frame superimposition ratio 305 indicating to what extent or an approximate ratio at which the normal frame 301 and the special frame 302 are superimposed.

It should be noted that although the superimposition ratio will be described later, the superimposition ratio of the normal frame 301 (normal frame superimposition ratio 305) and a superimposition ratio of the special frame 302 (denoted as a special frame superimposition ratio 306) are set such that the addition of the two produces 1.0 (100%). Therefore, the two are related such that when one of them is calculated, the other is automatically calculated.

It should be noted that although a description will be continued assuming a case in which the normal frame superimposition ratio 305 and the special frame superimposition ratio 306 are related such that the addition thereof produces 1.0 (100%), the present technology is still applicable even if the two are related in a different manner such as the addition produces, for example, 2.0.

Although a description will be continued assuming here that the normal frame superimposition ratio calculation section 402 calculates the normal frame superimposition ratio 305 with reference to the special frame 302, it is also possible to perform the processes described below by causing the normal frame superimposition ratio calculation section 402 to calculate the special frame superimposition ratio 306.

Also, it is also possible to perform the processes described below by causing the normal frame superimposition ratio calculation section 402 to calculate the normal frame superimposition ratio 305 and the special frame superimposition ratio 306 with reference to the special frame 302.

The normal frame superimposition ratio calculation section 402 can also be configured to perform some of the processes described below by causing the normal frame superimposition ratio calculation section 402 to calculate the special frame superimposition ratio 306 with reference to the special frame 302 and supplying a product of the calculated superimposition ratio and the special frame 302 (pixel value thereof) to the pixel value calculation section 401.

Also, the special frame 302 supplied to the normal frame superimposition ratio calculation section 402 may be a frame that has undergone a given filtering process. For example, the special frame 302 that has undergone an edge enhancement filtering process may be supplied to the normal frame superimposition ratio calculation section 402.

The normal frame 301 and the special frame 302 are supplied to the pixel value calculation section 401. Also, the normal frame superimposition ratio 305 calculated by the normal frame superimposition ratio calculation section 402 is supplied to the pixel value calculation section 401.

The pixel value calculation section 401 calculates a pixel value of a pixel of the superimposed frame 303 by adding together a pixel value of a target pixel of the normal frame 301 and a pixel value of a target pixel of the special frame 302. At the time of the addition, the product of the multiplication of the pixel value of the normal frame 301 by the normal frame superimposition ratio 305 and the product of the multiplication of the pixel value of the special frame 302 by the special frame superimposition ratio 306 are added together.

The above can be expressed by the following formula (1):

Pixel value of the superimposed frame 303=(pixel value of the normal frame 301)×(normal frame superimposition ratio 305)+(pixel value of the special frame 302)×(special frame superimposition ratio 306)    (1)

(special frame superimposition ratio 306)=1−(normal frame superimposition ratio 305)

It should be noted that the method by which the pixel value of the superimposed frame 303 is calculated here is merely an example, and the pixel value may be calculated on the basis of other formula.

It should be noted that the process based on the formula (1) is performed for each pixel, and the process is performed by using a pixel value corresponding to a color space applied.

For example, in a case of a YCbCr space, letting the pixel value of the normal frame 301 be denoted by (Ywl, Cbwl, Crwl), the pixel value of the special frame 302 be denoted by (Yfl, Cbfl, Crfl), and the pixel value of the superimposed frame 303 be denoted by (Yov, Cbov, Crov), and the normal frame superimposition ratio be denoted by R, the pixel value of the superimposed frame 303 is calculated as follows:

$Yov=R×Ywl+(1.0−R)×Yfl$ $Cbov=R×Cbwl+(1.0−R)×Cbfl$ $Crov=R×Crwl+(1.0−R)×Crfl$

It should be noted that in a case where the special frame 302 is one channel (monochrome image), the calculation is made assuming that Cbfl and Crfl are 0.

In the case of an RGB space, letting the pixel value of the normal frame 301 be denoted by (Rwl, Gwl, Bwl), the pixel value of the special frame 302 be denoted by (Rfl, Gfl, Bfl), and the pixel value of the superimposed frame 303 be denoted by (Rov, Gov, Bov), and the normal frame superimposition ratio be denoted by R, the pixel value of the superimposed frame 303 is calculated as follows:

$Rov=R×Rwl+(1.0−R)×Rfl$ $Gov=R×Gwl+(1.0−R)×Gfl$ $Bov=R×Bwl+(1.0−R)×Bfl$

It should be noted that in a case where the special frame 302 is one channel (monochrome image), the calculation is made assuming that the RGB values of the special frame 302 take on the same value, that is, $Rfl=Gfl=Bfl=Yfl$.

It should be noted that the present technology is applicable to a color space other than the YCbCr space and the RGB space cited here as examples, and calculations suitable for the color space are performed.

<Superimposition Ratio Defining Function>

A description will be added here regarding the superimposition control information 304. The superimposition control information 304 is, for example, information defined by the graph (will be denoted as a superimposition ratio defining function as appropriate) illustrated in FIG. 12.

Figure 12:
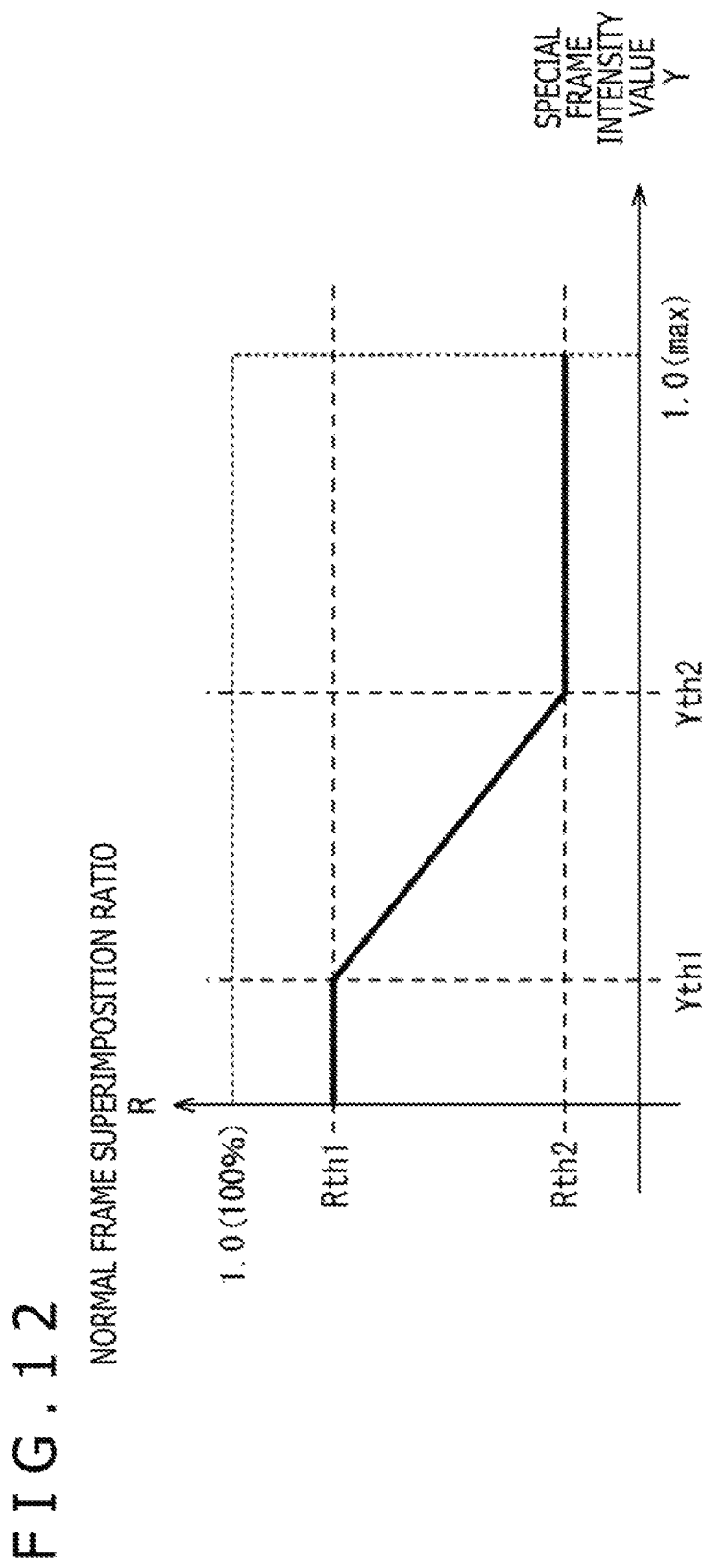
FIG. 12 is a diagram for describing a superimposition ratio defining function.

The graph illustrated in FIG. 12 depicts an intensity value Y of the special frame 302 along the horizontal axis and the normal frame superimposition ratio 305 along the vertical axis. Assume that the intensity value Y of the special frame 302 and the normal frame superimposition ratio 305 can take on a value between 0 and 1.0. For example, a pixel brightness value of the special frame can be used as the intensity value Y of the special frame 302.

A description will be added here regarding the intensity value Y. The special frame 302 (special image) is an image having a digital value proportional to a fluorescence intensity (brightness) and a single-channel monochrome image. Also, there are a case in which the special frame 302 has a single color and a case in which a color map proportional to the fluorescence intensity is assigned. In these cases, the special frame 302 is a color image.

In the case of a color image, the pixel value often has three channels, and various color spaces are possible such as RGB, YCbCr, L*a*b*, and L*u*v*.

The intensity value Y is defined from the special frame 302 described above. It is sufficient if the intensity value Y is correlated with the fluorescence intensity, and specifically, a brightness value or other value can be used. In the case of a monochrome image, the pixel value itself can be used as the intensity value Y. Also, in a case of a color image, a channel corresponding to the brightness may be used as the intensity value Y. Alternatively, a value calculated from a three-channel signal through mixture at an appropriate ratio may be used as the intensity value Y.

Referring to the graph illustrated in FIG. 12, a threshold Yth1 and a threshold Yth2 are set for the intensity value Y of the special frame 302. Also, a threshold Rth1 and a threshold Rth2 are set for the normal frame superimposition ratio 305. These thresholds Yth1, Yth2, Rth1, and Rth2 are used as the superimposition control information 304 and supplied to the normal frame superimposition ratio calculation section 402.

In the case where the intensity value Y of the supplied special frame 302 falls within a range between 0 and the threshold Yth1, the normal frame superimposition ratio calculation section 402 sets the threshold Rth1 as the normal frame superimposition ratio 305. That is, in a case where the intensity value Y<the threshold Yth1, the normal frame superimposition ratio 305=the threshold Rth1.

For example, in a case where the threshold Rth1 is 0.8, the normal frame superimposition ratio 305 is set to 0.8 and supplied to the pixel value calculation section 401. In such a case, the pixel value calculation section 401 superimposes the normal frame 301 and the special frame 302 at a 0.8:0.2 ratio.

Substituting the normal frame superimposition ratio 305 of 0.8 into the above formula (1), the pixel value of the superimposed frame 303=(the pixel value of the normal frame 301)×0.8+(the pixel value of the special frame 302)×0.2.

The pixel value of the superimposed frame 303 is calculated by such a computation.

Also, in a case where the intensity value Y of the supplied special frame 302 falls within a range between the threshold Yth1 and the threshold Yth2, the normal frame superimposition ratio calculation section 402 sets a value proportional to the intensity value Y as the normal frame superimposition ratio 305.

That is, in a case where the threshold Yth1 the intensity value Y<the threshold Yth2, the value R calculated by the following formula (2) is set as the normal frame superimposition ratio 305.

$$R = a \times Y + b$$

$$a=(Rth2-Rth1)/(Yth2-Yth1), b=Rth1-a \times Yth1 \quad (2)$$

The formula (2) is a linear function for finding the normal frame superimposition ratio 305 (=R). Although a description will be continued by taking, as an example, a case in which the value found by the linear function is used as the normal frame superimposition ratio 305 in a case where the threshold Yth1≤the intensity value Y<the threshold Yth2, it is also possible to use a function other than a linear function or a table associating the intensity value Y with the normal frame superimposition ratio 305 as will be described later.

For example, in a case where the normal frame superimposition ratio 305 is calculated to be 0.5 on the basis of the formula (2), the normal frame superimposition ratio 305 is set to 0.5 and supplied to the pixel value calculation section 401. In such a case, the pixel value calculation section 401 superimposes the normal frame 301 and the special frame 302 at a 0.5:0.5 ratio.

Substituting the normal frame superimposition ratio 305 of 0.5 into the above formula (1), the pixel value of the superimposed frame 303=(the pixel value of the normal frame 301)×0.5+(the pixel value of the special frame 302)×0.5.

The pixel value of the superimposed frame 303 is calculated by such a computation.

Also, in a case where the intensity value Y of the supplied special frame 302 falls within a range between the threshold Yth2 and 1.0, the normal frame superimposition ratio calculation section 402 sets the threshold Rth2 as the normal frame superimposition ratio 305. That is, in a case where the threshold Yth2≤the intensity value Y, the normal frame superimposition ratio 305=the threshold Rth2.

For example, in a case where the threshold Rth2 is 0.2, the normal frame superimposition ratio 305 is set to 0.2 and supplied to the pixel value calculation section 401. In such a case, the pixel value calculation section 401 superimposes the normal frame 301 and the special frame 302 at a 0.2:0.8 ratio.

Substituting the normal frame superimposition ratio 305 of 0.2 into the above formula (1), the pixel value of the superimposed frame 303=(the pixel value of the normal frame 301)×0.2+(the pixel value of the special frame 302)×0.8.

The pixel value of the superimposed frame 303 is calculated by such a computation.

As described above, the superimposition ratio (blending ratio) between the normal frame 301 and the special frame 302 is set by the intensity value Y of the special frame 302, thus preventing saturation of the signal level in the superimposed frame 303.

Figure 13:
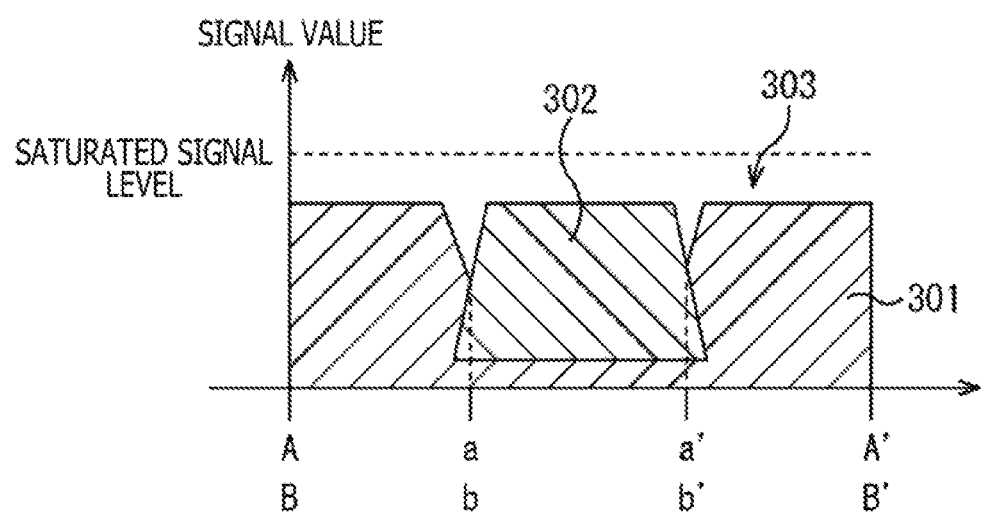
FIG. 13 is a diagram for describing a signal level after combining.

Reconsider, for example, a case in which the normal frame 301 and the special frame 302 as illustrated in FIG. 8 are acquired. In the case where the normal frame 301 and the special frame 302 as illustrated in FIG. 8 are superimposed by the superimposition processing section 126 illustrated in FIG. 11 by using the superimposition ratio defining function illustrated in FIG. 12, the superimposed frame 303 having a signal level as illustrated in FIG. 13 is generated.

The blood vessel in the portion a-a' and the blood vessel in the portion b-b' are superimposed. In a portion where the intensity value Y of the special frame 302 is large as in this case, the superimposition ratio of the special frame 302 is set high, whereas the superimposition ratio of the normal frame 301 is set low. This prevents the signal level of the superimposed frame 303 from exceeding the saturation signal level.

Therefore, although there is a possibility that detailed information may be lost due, for example, to blown out highlights as a result of the signal level exceeding the saturation signal level as described with reference to FIG. 9, the present technology can prevent such a situation from occurring.

For example, if the superimposition leads to a signal level beyond the saturation signal level despite the fact that a plurality of blood vessels are captured in the special frame 302, there is a possibility that the plurality of blood vessels may become unidentifiable, resulting in loss of detailed information. However, the present technology ensures that the plurality of blood vessels captured in the special frame 302 are presented to the user in an identifiable manner, thus allowing for presentation of detailed information.

Also, in the portion other than the portion a-a' (b-b'), in other words, the portion where the intensity value Y of the special frame 302 is small, the superimposition ratio of the special frame 302 is set low, whereas the superimposition ratio of the normal frame 301 is set high. This makes it possible to prevent the signal level of the normal frame 301 from being inadvertently set low.

That is, the present technology superimposes the normal frame 301 and the special frame 302 in such a manner as to ensure that the signal level remains under the saturation signal level and superimposes the two frames at a varying mixing ratio instead of doing so at a constant mixing ratio.

Therefore, as described with reference to FIG. 10, if the normal frame 301 and the special frame 302 are superimposed at a constant mixing ratio, there is a possibility that the normal image 301 including peripheral information (e.g., information regarding a periphery of an affected site) may become dark, possibly resulting in an image deprived of detailed peripheral information. However, the present technology can prevent such a situation from occurring.

For example, it is possible to provide, to the user, the superimposed frame 303 that includes an image based on the normal frame 301 with no reduced brightness value in portions other than the portion a-a' (b-b'), in other words, in portions with no image based on the special frame 302 such as blood vessel image or in a periphery of such a blood vessel. This makes it possible to generate and provide, to the user, the superimposed frame 303 capable of presenting detailed peripheral information.

By applying the present technology, it is possible to superimpose normal and special frames without losing detailed information.

Referring again to FIG. 13 and regarding the signal range as a brightness component, it appears as if brightness and contrast have been reduced because of loss of a difference in brightness between the normal frame 301 and the special frame 302. In reality, however, the special frame 302 uniformly has colors inexistent among biological colors such as green and cyan, for example. Therefore, a sufficient color contrast remains, thus realizing superimposition free from signal saturation while maintaining visibility.

Incidentally, although it has been described that the superimposition ratio is defined by the superimposition ratio defining function illustrated in FIG. 12, the superimposition ratio may be set (calculated) by a function different from the superimposition ratio defining function illustrated in FIG. 12.

Figure 14:
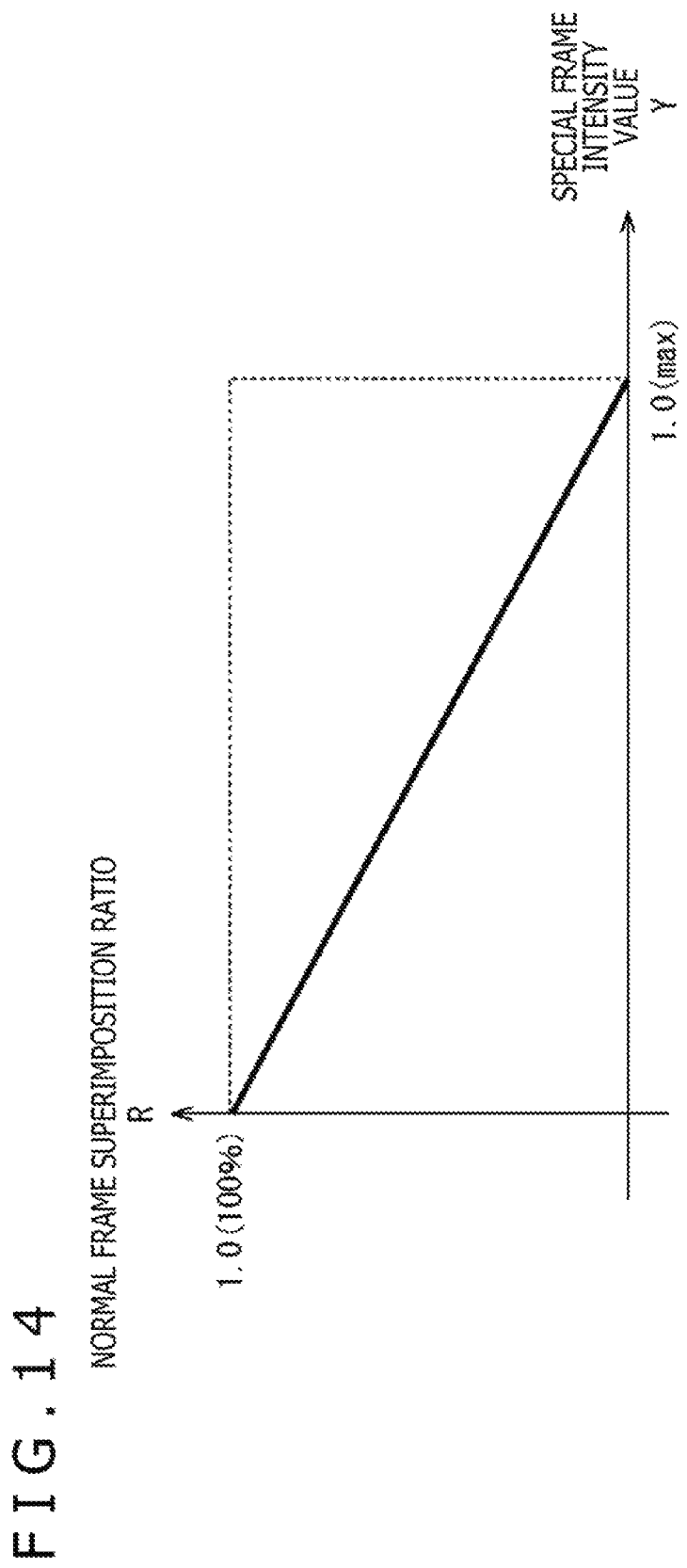
FIG. 14 is a diagram for describing the superimposition ratio defining function.

For example, the superimposition ratio defining function illustrated in FIG. 14 can be used. The superimposition ratio defining function illustrated in FIG. 14 is a function defined by a linear function between 0 and 1.0 without setting any thresholds for the intensity value Y of the special frame 302 and the normal frame superimposition ratio 305.

It is sufficient if the superimposition ratio defining function is such that when the intensity value Y of the special frame 302 is high, the superimposition ratio of the special frame 302 is high, and that when the intensity value Y of the special frame 302 is low, the superimposition ratio of the special frame is low.

However, it is probable that the normal frame 301 and the special frame 302 can be superimposed more properly by using the superimposition ratio defining function illustrated in FIG. 12 rather than the superimposition ratio defining function illustrated in FIG. 14. A description will be given of advantageous effects produced by setting the thresholds Yth1 and Yth2 for the intensity value Y of the special frame 302 and the thresholds Rth1 and Rth2 for the normal frame superimposition ratio 305 as in the superimposition ratio defining function illustrated in FIG. 12.

A description will be also given of advantageous effects of using the thresholds Yth1, Yth2, Rth1, Rth2 as the superimposition control information 304 and supplying the superimposition control information 304 to the normal frame superimposition ratio calculation section 402. That is, a case will be described in which the superimposition control information 304 is variable rather than fixed together with advantageous effects thereof.

Figure 15:
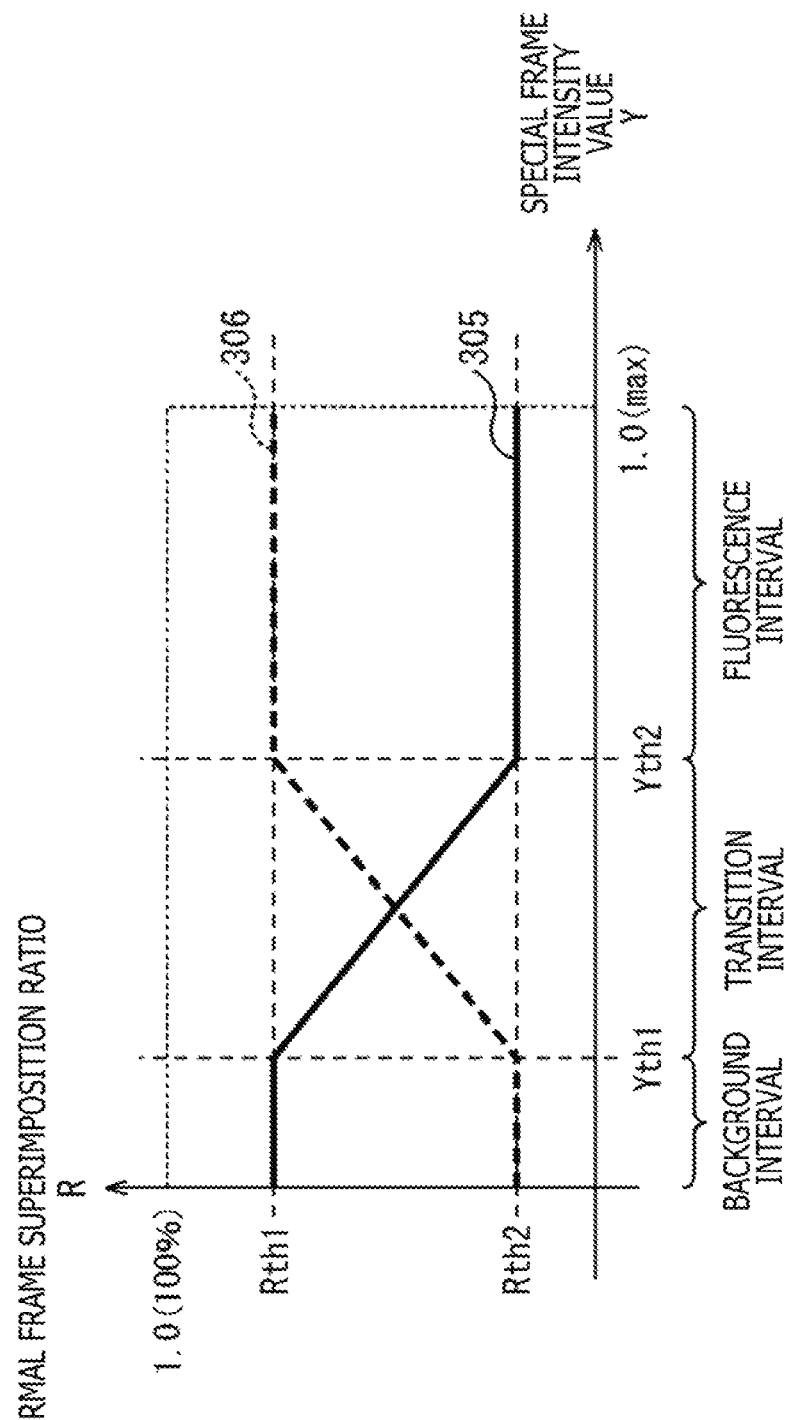
FIG. 15 is a diagram for describing the superimposition ratio defining function.

FIG. 15 illustrates again the superimposition ratio defining function illustrated in FIG. 12. Also, FIG. 15 illustrates the normal frame superimposition ratio 305 and the special frame superimposition ratio 306 together. The normal frame superimposition ratio 305 is depicted by a solid line whereas the special frame superimposition ratio 306 is depicted by a dotted line.

The normal frame superimposition ratio 305 and the special frame superimposition ratio 306 are related such that (the normal frame superimposition ratio 305)+(the special frame superimposition ratio 306)=1.0 is satisfied. Therefore, the normal frame superimposition ratio 305 and the special frame superimposition ratio 306 are expressed in a graph as illustrated in FIG. 15.

It should be noted that a case in which fluorescence observation that acquires an image by irradiating excitation light is performed as special light observation and a case in which the special frame 302 is a frame (image) acquired during fluorescence observation will be taken as examples.

In the case where the special frame intensity value Y<the threshold Yth1, the special frame 302 is a frame with no fluorescence or with an extremely small fluorescence signal. An interval during which the special frame intensity value Y<the threshold Yth1 will be referred to as a background interval.

During the background interval, the normal frame 301 is predominant in the superimposed frame 303. In other words, the normal frame 301 in the background is visible as opposed to the special frame 302 in the superimposed frame 303.

On the other hand, in a case where the threshold Yth2≤the special frame intensity value Y, the special frame 302 has sufficient fluorescence. An interval during which the threshold Yth2≤the special frame intensity value Y will be referred to as a fluorescence interval.

During the fluorescence interval, the special frame 302 is predominant in the superimposed frame 303. In other words, the special frame 302 is more visible than the normal frame 301 in the superimposed frame 303 during the fluorescence interval.

An interval between the background interval and the fluorescence interval will be referred to as a transition interval. During this transition interval, the threshold Yth1<the special frame intensity value Y<the threshold Yth2, and a transition is made from a state in which the normal frame 301 is predominant to a state in which the special frame 302 is predominant.

The transition interval varies in appropriate length depending on a purpose of fluorescence observation and should preferably be adjusted properly. That is, the thresholds Yth1 and Yth2 of the intensity value Y of the special frame 302 should preferably be set to appropriate values depending on the purpose of fluorescence observation. In other words, the thresholds Yth1 and Yth2 of the intensity value Y of the special frame 302 should preferably be variable.

For this reason, in the present embodiment, the thresholds Yth1 and Yth2 of the intensity value Y of the special frame 302 are supplied to the normal frame superimposition ratio calculation section 402 as the superimposition control information 304 as illustrated in FIG. 11. Such a configuration allows for the superimposition control information 304 suitable for the purpose of fluorescence observation to be supplied to the normal frame superimposition ratio calculation section 402.

For example, the user (practitioner) can be given the option to select a purpose of fluorescence observation such that the superimposition control information 304 that fits the selection is supplied to the normal frame superimposition ratio calculation section 402.

Also, setting the thresholds Rth1 and Rth2 for the normal frame superimposition ratio 305 makes it possible to perform the control described below. That is, in the background interval during which the normal frame 301 is predominant or in the fluorescence interval during which the special frame 302 is predominant, each of the normal frame 301 and the special frame 302 is present albeit at a minute level, and there is a case in which even such a minute amount of information is desirably left undeleted. In such a case, setting the thresholds Rth1 and Rth2 makes it possible to respond to such a demand.

That is, referring to FIG. 15, in a case where, for example, the intensity value Y of the special frame 302 is 0 (during the background interval), the normal frame superimposition ratio 305 is set to the threshold Rth1. In this case, the special frame superimposition ratio 306 is equal to (1.0–threshold Rth1) and is not 0. Also, during the background interval, there is no possibility for complete absence of superimposition of the special frame 302, and in a case where the special frame 302 has a minute amount of information, it is possible to reflect that minute amount of information into the superimposed frame 303 without deleting the information.

Similarly, referring to FIG. 15, in a case where, for example, the intensity value Y of the special frame 302 is 1.0 (during the fluorescence interval), the normal frame superimposition ratio 305 is set to the threshold Rth2. Also, during the fluorescence interval, there is no possibility for complete absence of superimposition of the normal frame 301, and in a case where the normal frame 301 has a minute amount of information, it is possible to reflect that minute amount of information into the superimposed frame 303 without deleting the information.

As described above, setting the thresholds Rth1, Rth2, Yth1, and Yth2 makes it possible, for example, to tailor the superimposition control information 304 to suit the purpose of fluorescence observation, thereby allowing for proper superimposition process and generating the superimposed frame 303 that provides detailed information to the user in a clearer manner.

Figure 16:
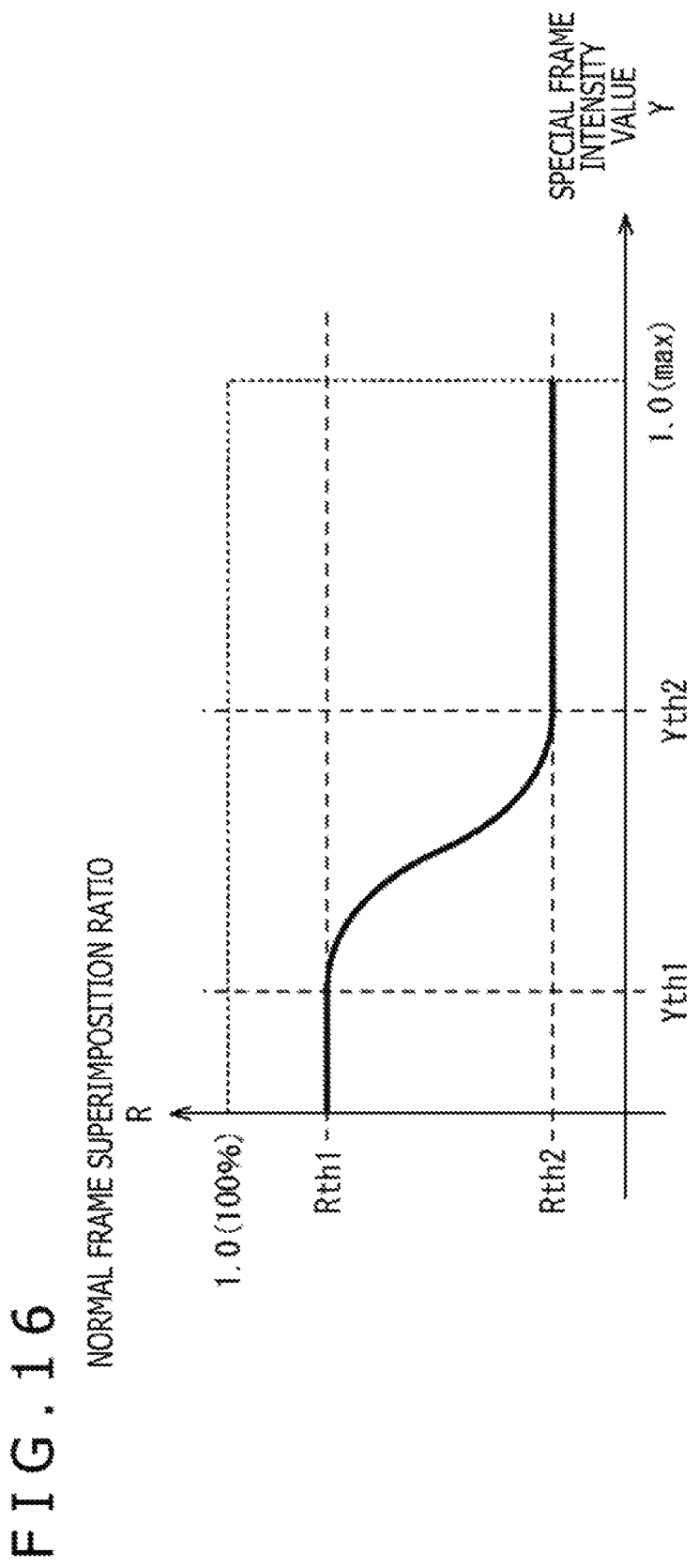
FIG. 16 is a diagram for describing the superimposition ratio defining function.

In the case where the thresholds Rth1, Rth2, Yth1, and Yth2 are variable, a superimposition ratio defining function as illustrated in FIG. 16 may be used to provide a smoother change from the background interval, to the transition interval, and to the fluorescence interval.

In the superimposition ratio defining function as illustrated in FIG. 16, a smooth change in the normal frame superimposition ratio 305 before and after the threshold Yth1 is defined by a curve. Also, a smooth change in the normal frame superimposition ratio 305 before and after the threshold Yth2 is defined by a curve.

Such a superimposition ratio defining function may be used. Also, although not illustrated, a superimposition ratio defining function defined by an S-shaped curve may be used, and the application of the present technology is not limited to a superimposition ratio defining function defined by a line graph.

<Adjustment of Superimposition Control Information>

A description will be given next of setting (adjustment) of the superimposition control information 304 by citing specific examples as described above.

Specific Example 1

Figure 17:
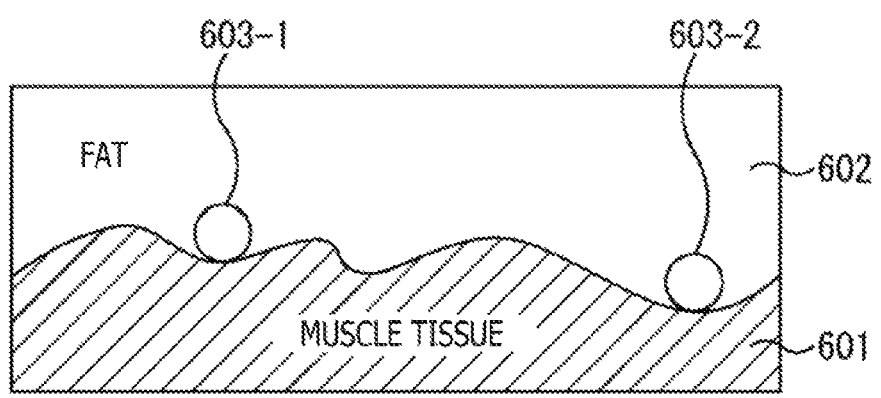
FIG. 17 is a diagram for describing an image to be captured.

As a specific example 1, a case will be described in which a blood vessel in a superficial layer of a tissue as illustrated in FIG. 17 is observed. FIG. 17 depicts the blood vessel in the superficial layer of the tissue as seen from sideways, with a muscle tissue 601 located at the bottom in FIG. 17 and a fat 602 located on top thereof. Also, lymphatic nodes 603-1 and 603-2 are present between the muscle tissue 601 and the fat 602.

In the case where the lymphatic nodes 603 in the fat 602 as illustrated in FIG. 17 are observed through ICG fluorescence observation, the lymphatic nodes 603 emit fluorescence at deep positions in the fat 602, and this state is captured with a camera from outside the superficial layer of the tissue (outside the fat 602 in FIG. 17). Therefore, a difficult-to-see image is probably due to low fluorescence intensity. In other words, it is likely that the special frame 302 acquired will be dark and that the lymphatic nodes 603 are difficult to see in the image.

Figure 18:
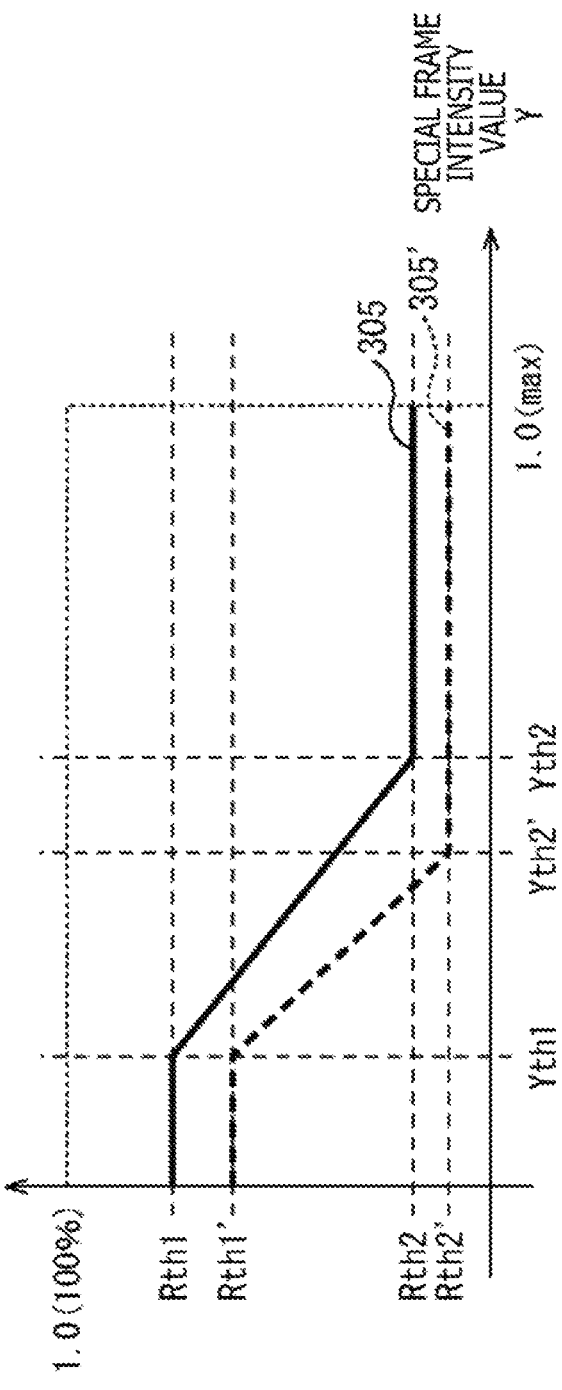
FIG. 18 is a diagram for describing the superimposition ratio defining function.

For this reason, in a case where such blood vessels in a superficial layer of a tissue are observed, a superimposition ratio defining function as illustrated in FIG. 18 is used. The superimposition ratio defining function depicted by a solid line in FIG. 18 is the superimposition ratio defining function illustrated in FIG. 12 for comparison. Hereinafter, the superimposition ratio defining function illustrated in FIG. 12 and illustrated for comparison will be denoted as the superimposition ratio defining function 305.

Also, a superimposition ratio defining function 305' depicted by a dotted line in FIG. 18 illustrates a superimposition ratio defining function suitable for observation of blood vessels in a superficial layer of a tissue as illustrated in FIG. 17. Also, the superimposition ratio defining function 305 and the superimposition ratio defining function 305' are functions for setting the normal frame superimposition ratio 305 as in the case described above.

In the case where there is a possibility that the special frame 302 may become dark, the fluorescence interval is extended due to a low fluorescence intensity. In other words, in a case where there is a possibility that the special frame 302 may become dark, the maximum value that can be taken on by the intensity value Y of the special frame 302 is highly likely smaller than 1.0. Therefore, it is likely that the superimposition ratio defining function 305 whose threshold Yth2 is set such that the maximum value that can be taken on by the intensity value Y of the special frame 302 is 1.0 may be unable to set an appropriate superimposition ratio.

For this reason, as the maximum value that can be taken on by the intensity value Y of the special frame 302 decreases, the threshold Yth2 set on the maximum value side is also set to a small value. That is, as illustrated in FIG. 18, a threshold Yth2' of the superimposition ratio defining function 305' is set to a value smaller than the threshold Yth2 of the superimposition ratio defining function 305.

Suppose, for example, that, in a case where blood vessels in a superficial layer of a tissue illustrated in FIG. 17 are observed, the maximum value that can be taken on by the intensity value Y of the special frame 302 is equivalent to the threshold Yth2'. Supposing, in such a case, that superimposition is performed by applying the superimposition ratio defining function 305, the special frame superimposition ratio 306 of the special frame 302 does not take on the maximum value even if the special frame 302 is the threshold Yth2' (the normal frame superimposition ratio 305 of the normal frame 301 does not take on a minimum value).

Therefore, there is a possibility that the blending ratio of the special frame 302 may decrease. That is, if the superimposition ratio defining function 305 is applied, there is a possibility that the special frame superimposition ratio 306 may not reach its maximum value even when the intensity value Y of the special frame 302 takes on its maximum possible value. If such a condition takes place, there is a possibility that the amount of information from the special frame 302 in the superimposed frame 303 may decrease.

However, if the superimposition ratio defining function 305' is applied, the special frame superimposition ratio 306 reaches its maximum value when the special frame 302 is the threshold Yth2'. Therefore, the blending ratio of the special frame 302 will increase, thus maintaining constant the amount of information from the special frame 302 in the superimposed frame 303.

Therefore, it is possible to eliminate the likelihood for reduction in amount of information from the special frame 302 in the superimposed frame 303 by applying the superimposition ratio defining function 305'.

As described above, in a case where the blood vessels in a superficial layer of a tissue as illustrated in FIG. 17 are observed, the superimposition ratio defining function 305' is applied in which the threshold Yth2' of the intensity value Y of the special frame 302 is set to a small value.

Also, referring to FIG. 18, the value of the threshold Rth2 of the normal frame superimposition ratio 305 in the superimposition ratio defining function 305' has been changed to a small value. As described above, it is possible to decrease the superimposition ratio of the normal frame 301, increase the superimposition ratio of the special frame 302, and achieve superimposition in such a manner as to display the special frame 302 in a more highlighted manner by setting the threshold Rth2' of the superimposition ratio defining function 305' to a small value during the fluorescence interval.

Further, referring to FIG. 18, the value of the threshold Rth1 of the normal frame superimposition ratio 305 in the superimposition ratio defining function 305' has been changed to a small value. As described above, the ratio at which the normal frame 301 is superimposed with the special frame 302 is reduced during the background interval by setting the threshold Rth1' of the normal frame superimposition ratio 305 to a small value.

In other words, during the background interval, the threshold Rth1' of the normal frame superimposition ratio 305 is also set to a small value to reduce the superimposed component of the normal frame 301 and render the fluorescence state captured in the special frame 302 more highlighted.

As described above, by setting the threshold Rth1' of the superimposition ratio defining function 305 to a small value as well, in other words, by setting the special frame superimposition ratio 306 to a large value during the background interval, it is possible to increase the ratio at which the special frame 302 is superimposed during the background interval. Even if the special frame 302 has a low fluorescence state, it is possible to achieve superimposition while ensuring that information of the special frame 302 is not covered by the normal frame 301.

Specific Example 2

Figure 19:
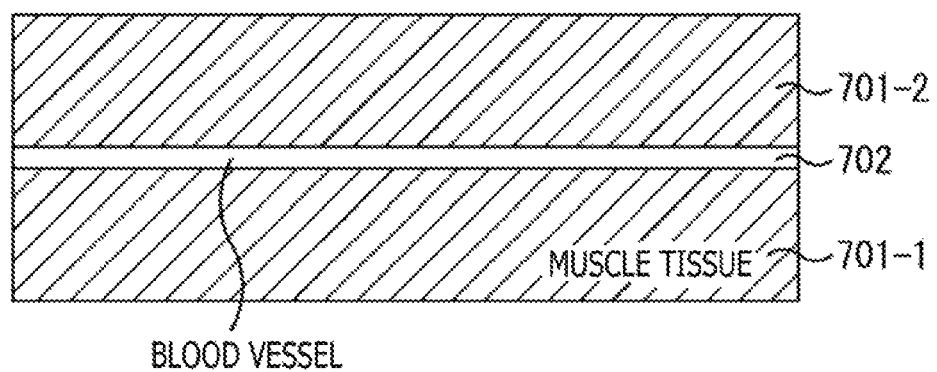
FIG. 19 is a diagram for describing an image to be captured.

A description will be given of a case in which a blood vessel in a deep area of a muscle tissue as illustrated in FIG. 19 is observed as a specific example 2. FIG. 19 depicts the blood vessel in the deep area of the muscle tissue as seen from sideways, with a muscle tissue 701-1 located at the bottom in FIG. 19, a blood vessel 702 on top thereof, and a muscle tissue 701-2 located further on top thereof.

In the case where the blood vessel 702 in the muscle tissues 701 as illustrated in FIG. 19 is observed through ICG fluorescence observation, the blood vessel 702 emits fluorescence at a deep position in the muscle tissues 701, and this state is captured with a camera from outside the muscle tissue (outside the muscle tissue 701-2 in FIG. 19). Therefore, a difficult-to-see frame is probably due to low fluorescence intensity. In other words, it is likely that the special frame 302 acquired will be dark and that the blood vessel 702 is difficult to see in the image.

Figure 20:
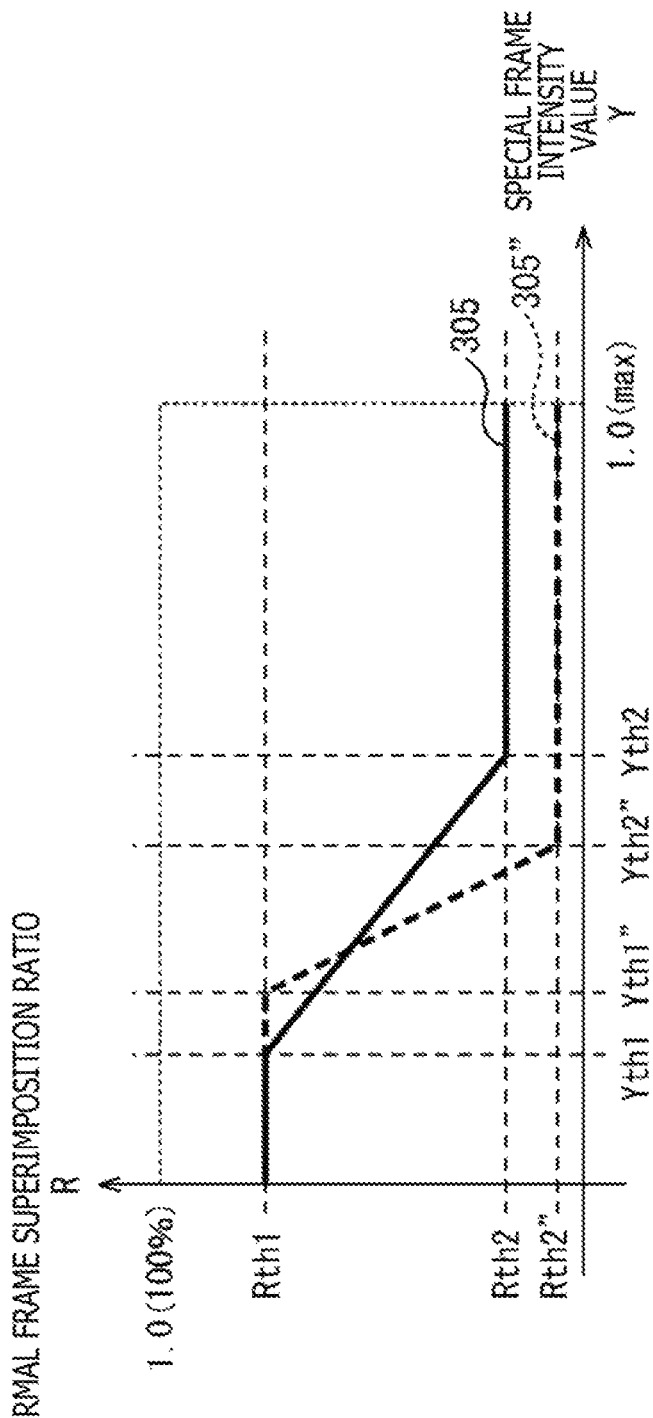
FIG. 20 is a diagram for describing the superimposition ratio defining function.

For this reason, in a case where such a blood vessel in a deep area of a muscle tissue is observed, a superimposition ratio defining function as illustrated in FIG. 20 is used. The superimposition ratio defining function depicted by a solid line in FIG. 20 is the superimposition ratio defining function illustrated in FIG. 12 for comparison and will be denoted as the superimposition ratio defining function 305.

Also, the superimposition ratio defining function 305' depicted by a dotted line in FIG. 20 illustrates a superimposition ratio defining function suitable for observation of a blood vessel in a deep area of a muscle tissue as illustrated in FIG. 19. Also, the superimposition ratio defining function 305 and the superimposition ratio defining function 305' are functions for setting the normal frame superimposition ratio 305 as in the case described above.

In the case where there is a possibility that the special frame 302 may become dark, the maximum value that can be taken on by the intensity value Y of the special frame 302 is highly likely smaller than 1.0 due to a low fluorescence intensity as in the case described as the specific example 1. Therefore, in keeping with the decrease in the maximum value that can be taken on by the intensity value Y of the special frame 302, the threshold Yth2 set on the maximum value side is also set to a small value. That is, as illustrated in FIG. 20, a threshold Yth2" of a superimposition ratio defining function 305" is set to a value smaller than the threshold Yth2 of the superimposition ratio defining function 305.

As described above, it is possible to eliminate the likelihood for reduction in amount of information from the special frame 302 in the superimposed frame 303 as in the case described above as the specific example 1 by setting the threshold Yth2" of the superimposition ratio defining function 305" to a small value.

As described above, in a case where a blood vessel in a deep area of a muscle tissue as illustrated in FIG. 19 is observed, the superimposition ratio defining function 305" is applied whose threshold Yth2 of the intensity value Y of the special frame 302 is set to a small value.

Also, referring to FIG. 20, in the superimposition ratio defining function 305", a threshold Rth2" of the normal frame superimposition ratio 305 has also been changed to a small value. As described above, it is possible to reduce the superimposition ratio of the normal frame 301, increase the superimposition ratio of the special frame 302, and achieve superimposition in such a manner as to display the special frame 302 in a more highlighted manner by setting the threshold Rth2" of the normal frame superimposition ratio 305" to a small value during the fluorescence interval.

Further, referring to FIG. 20, in the superimposition ratio defining function 305", a threshold Yth1" of the intensity value Y of the special frame 302 has also been changed to a large value. As described above, in a case where the special frame 302 is a minute signal, it is possible to ensure that information of the normal frame 301 remains unaffected by information of such a minute signal by setting the threshold Yth1" of the intensity value Y of the special frame 302 to a large value.

For example, a possible case where the special frame 302 is a minute signal is a signal affected by scattered light. In order to reduce, of the fluorescence state captured in the special frame 302, the effect of scattered light, the threshold Yth1" of the intensity value Y of the special frame 302 is set to a large value.

Although it is probably desirable to be able to observe the blood vessel 702 in the muscle tissue 701 with only the area of the blood vessel 702 highlighted when the blood vessel 702 in the muscle tissue 701 is observed through fluorescence observation, edge portions of the blood vessel 702 may become blurred in the periphery of the blood vessel 702 due to the effect of scattered light.

For this reason, as described above, it is possible to maintain intact information regarding the periphery acquired from the normal frame 301 by setting the threshold Yth1" of the intensity value Y of the special frame 302 to a large value. That is, it is possible to achieve superimposition in such a manner that a surrounding area of the blood vessel with minute scattered light is regarded as a background.

In the case where, from the specific examples 1 and 2, the region of interest (e.g., lymph node or blood vessel) in the special frame 302 likely has a low fluorescence state, it is possible to achieve superimposition without reducing information acquired from the special frame 302 by adjusting the threshold Yth2, the larger threshold of the intensity value Y of the special frame.

Also, in a case where the region of interest (e.g., lymph node or blood vessel) in the special frame 302 probably has a low fluorescence state, it is possible to achieve superimposition in such a manner that the information from the special frame 302 is highlighted in the image by adjusting the threshold Rth2, the smaller threshold of the normal frame superimposition ratio 305.

Also, in a case where an effect (e.g., effect of scattered light) caused by a light emission state of a region other than the region of interest (e.g., lymph node or blood vessel) in the special frame 302 is probably present, it is possible to achieve superimposition with reduced effect of the special frame 302 but without reducing information acquired from the normal frame 301 during the background interval by adjusting the threshold Yth1 which is a smaller value to be set as the intensity value Y of the special frame 302.

Also, in a case where the region of interest (e.g., lymph node or blood vessel) in the special frame 302 probably has a low fluorescence state, it is possible to achieve superimposition without reducing information acquired from the special frame 302 even during the background interval where the normal frame 301 is predominant by adjusting the threshold Rth1, the larger threshold of the normal frame superimposition ratio 305.

Specific Example 3

A description will be given of a case in which a superimposition ratio defining function whose transition interval has been shortened by adjusting the thresholds Yth1 and Yth2 of the intensity value Y of the special frame 302 is used as a specific example 3.

Figure 21:
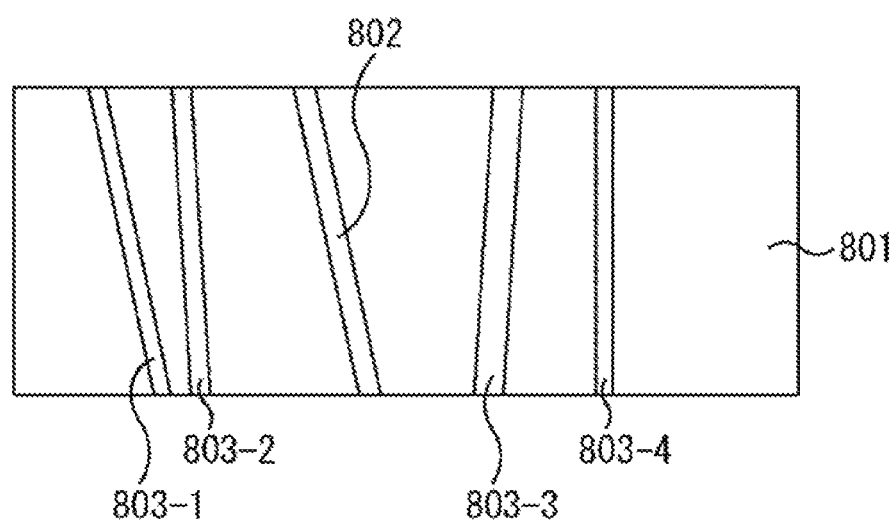
FIG. 21 is a diagram for describing an image to be captured.

A case will be described in which a biliary tract and urinary tracts as illustrated in FIG. 21 are observed. FIG. 21 illustrates a state in which a biliary tract 802 and a plurality of blood vessels 803-1 to 803-4 are located in a muscle tissue 801. Assume that FIG. 21 illustrates, for example, an image captured as the normal frame 301.

Biliary tracts and urinary tracts are similar to blood vessels in shape and color, and from an image captured with the normal frame 301 alone, the image appears as illustrated in FIG. 21, and it is difficult to distinguish between the biliary tract 802 and the blood vessel 803. At a time like this, there is a case in which the biliary tract 802 is observed through fluorescence observation.

For example, probable tasks to be undertaken include comparing the normal frame 301 and the special frame 302, determining that the portion of the special frame 302 emitting fluorescence is the biliary tract 802, identifying the area of the normal frame 301 corresponding to the determined area, and acquiring information regarding the periphery of the biliary tract 802.

That is, fluorescence observation may be conducted to confirm a tract to be distinguished (e.g., biliary tract or urinary tract) on the basis of whether or not fluorescence is emitted. In such a case, it is likely preferable that an area that emits fluorescence and another area that does not emit fluorescence can be distinguished between with accuracy.

Figure 22:
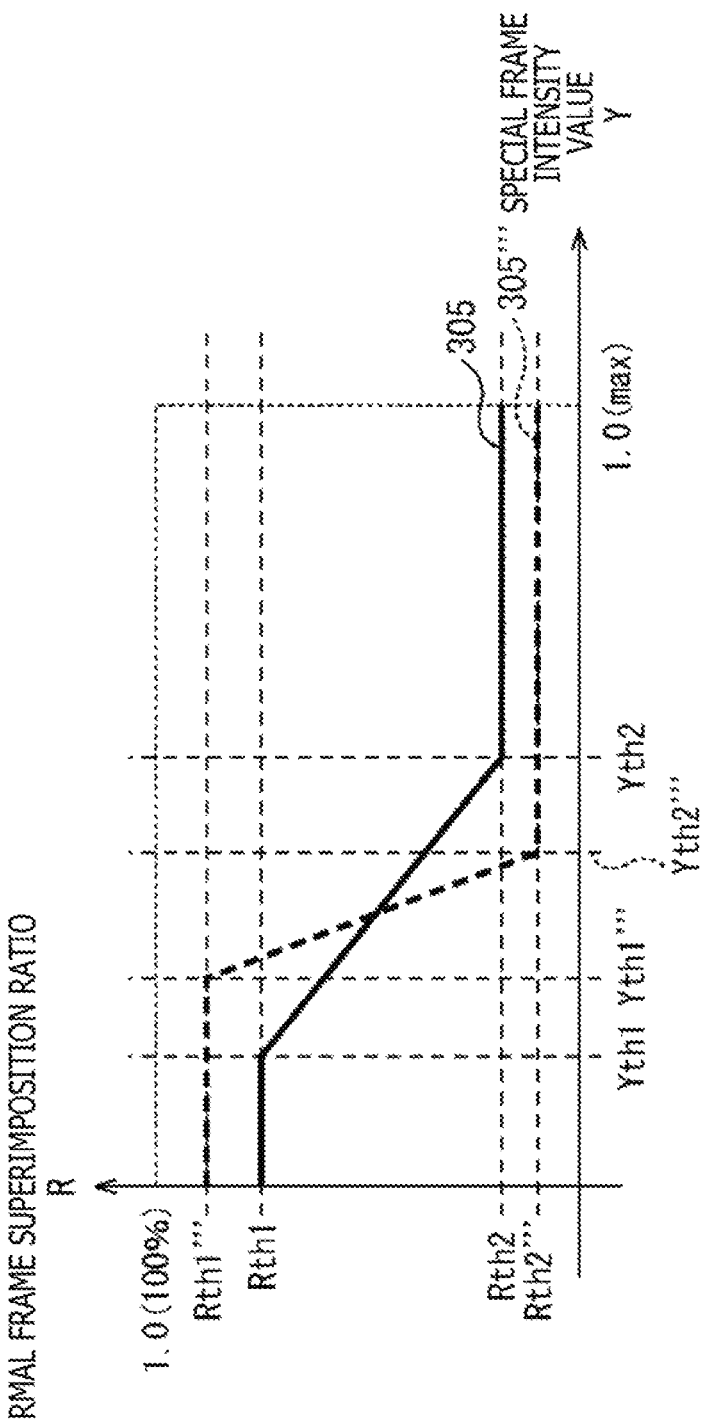
FIG. 22 is a diagram for describing the superimposition ratio defining function.

For this reason, a superimposition ratio defining function 305''' as illustrated in FIG. 22 is applied. The superimposition ratio defining function 305''' as illustrated in FIG. 22 is a function with a shorter transition interval. The transition interval is an interval during which a transition is made from the state in which the normal frame 301 is predominant to the state in which the special frame 302 is predominant.

There is a possibility that when fluorescence observation is performed to determine whether or not fluorescence is emitted, such a determination may be difficult to make during the transition interval. Therefore, the superimposition ratio defining function 305''' as illustrated in FIG. 22 is applied to shorten the transition interval and present, to the user, the superimposed frame 303 with which it is easy to determine whether or not fluorescence is emitted.

In the superimposition ratio defining function 305''' as illustrated in FIG. 22, a threshold Yth1''' of the intensity value Y of the special frame 302 is set to a large value, and a threshold Yth2''' thereof is set to a small value. Such settings provide a short transition interval.

Also, in the superimposition ratio defining function 305''' as illustrated in FIG. 22, a threshold Rth1''' of the normal frame superimposition ratio 305 is set to a large value, and a threshold Rth2''' thereof is set to a small value. Such settings provide a superimposition ratio defining function having a steep slope during the transition interval.

As described above, it is possible to achieve superimposition with no reduction in information from the special frame 302 by setting the threshold Yth2''' of the intensity value Y of the special frame 302 to a small value even if there is a possibility that the maximum value that can be taken on by the intensity value Y of the special frame 302 may decrease during the fluorescence interval. Therefore, even if an area emits fluorescence with low intensity, it is possible to present, to the user, that the area emits fluorescence on the superimposed frame 303.

Also, it is possible, during the fluorescence interval, to reduce the superimposition ratio of the normal frame 301, increase the superimposition ratio of the special frame 302, and achieve superimposition in such a manner as to display the special frame 302 in a more highlighted manner by setting the threshold Rth2''' of the normal frame superimposition ratio 305 to a small value during the fluorescence interval. Therefore, an area that emits fluorescence can be presented to the user in a more highlighted manner as a fluorescence-emitting area on the superimposed frame 303.

Also, it is possible to achieve superimposition with reduced information from the special frame 302 even in the presence of a minute signal in the special frame 302 during the background interval by setting the threshold Yth1''' of the intensity value Y of the special frame 302 to a large value and the threshold Rth1''' of the normal frame superimposition ratio 305 to a large value. Therefore, superimposition can be achieved without giving any unnecessary information to the user in areas with no fluorescence.

As described above, the thresholds Yth1, Yth2, Rth1, and Rth2 can be set properly according to the purpose of fluorescence observation. Also, the thresholds Yth1, Yth2, Rth1, and Rth2 that can be set properly are supplied to the superimposition processing section 126 as the superimposition control information 304, thus allowing for superimposition using the superimposition control information 304 tailored to the purpose of use and generation of a superimposed frame tailored to the purpose of use.

<Processes Performed by Superimposition Processing Section>

Figure 23:
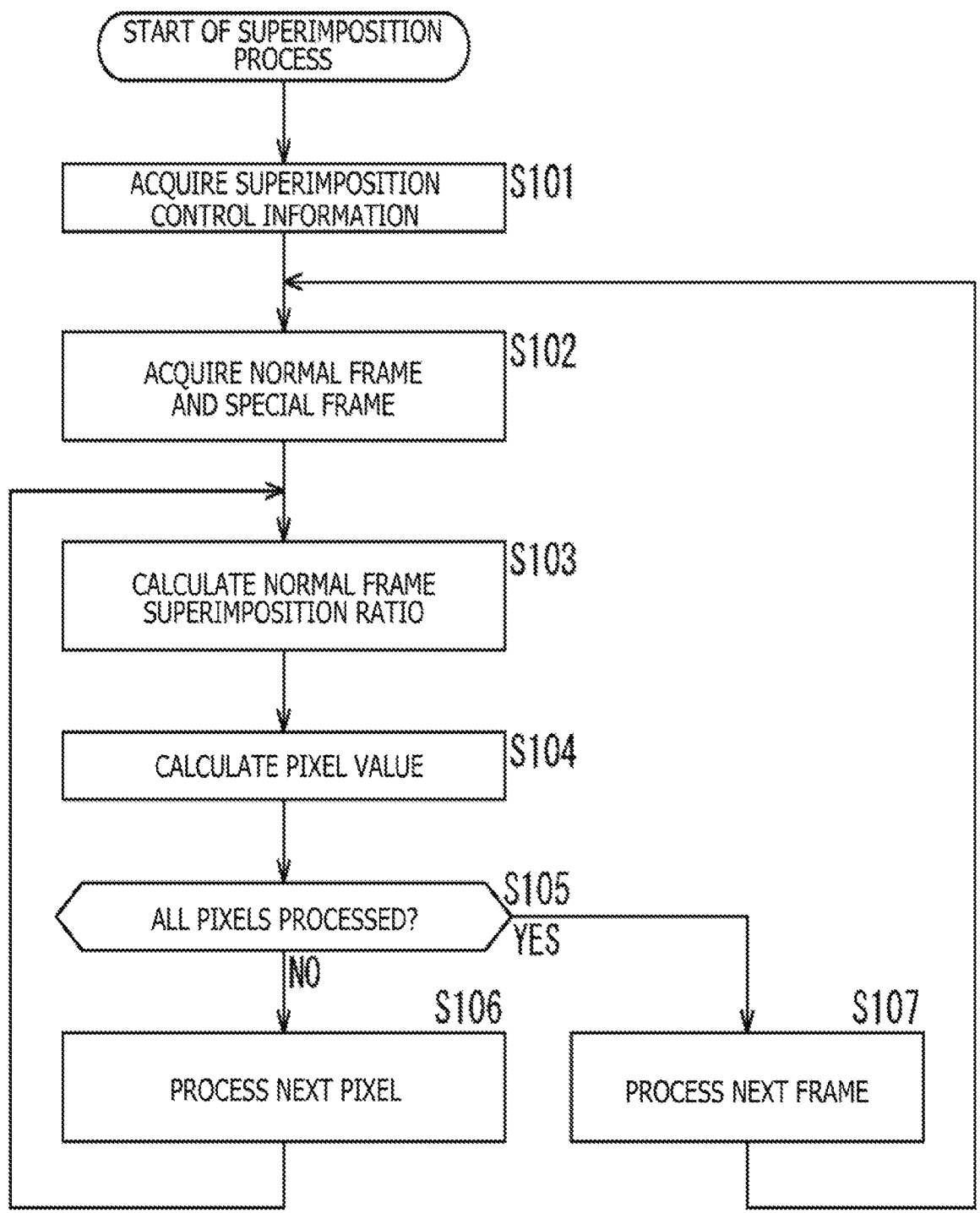
FIG. 23 is a flowchart for describing a superimposition process.

A description will be added next regarding the processes performed by the superimposition processing section 126 (FIG. 11) with reference to the flowchart illustrated in FIG. 23.

In step S101, the superimposition processing section 126 acquires the superimposition control information 304. For example, a purpose of use is selected by the user, and the superimposition control information 304 suitable for the purpose of use is selected and supplied.

In step S102, the superimposition processing section 126 acquires the normal frame 301 and the special frame 302. The acquired normal frame 301 is supplied to the pixel value calculation section 401, and the special frame 302 is supplied to the pixel value calculation section 401 and the normal frame superimposition ratio calculation section 402.

It should be noted that although the special frame 302 has been described by taking, as an example, a case in which the normal frame 301 and the special frame 302 are switched every frame in a time-divided manner as described with reference to FIGS. 3 to 7, the present technology is not limited to the manner in which the special frame 302 is acquired. The present technology is applicable even if the special frame 302 is generated and acquired in a manner different from that described above.

For example, the normal frame 301 and the special frame 302 may be acquired by irradiating light including a mixture of visible light and excitation light, splitting reflected light from a subject using a beam splitter, a dichroic mirror, or other means at a given wavelength, and detecting two beams separately with two sensors, one for a beam including excitation light and another for a beam including visible light. The present technology is also applicable in a case where the normal frame 301 and the special frame 302 are acquired by such a mechanism.

Also, the normal frame 301 and the special frame 302 may be acquired by changing the sensor's color filter and rendering pixels sensitive, for example, only to the IR wavelength band. In this case, light including a mixture of visible light and excitation light is irradiated, and only excitation light returning as reflected light is cut off, for example, with an excitation light-cutting filter, thus allowing the normal frame 301 to be acquired by the R, G, and B pixels and the special frame 302 to be acquired by the IR pixels. The present technology is also applicable in a case where the normal frame 301 and the special frame 302 are acquired by such a mechanism.

Any method other than the above can be applied to the present technology as long as the normal frame 301 and the special frame 302 can be acquired with a certain simultaneity. The present technology is applicable when the superimposed frame 303 is generated after acquisition of the normal frame 301 and the special frame 302.

Returning to the description with reference to the flowchart illustrated in FIG. 23, in step S103, the normal frame superimposition ratio 305 is calculated by the normal frame superimposition ratio calculation section 402 by means of the process as described above. The calculated normal frame superimposition ratio 305 is supplied to the pixel value calculation section 401.

In step S104, the pixel value at the time of superimposition of the normal frame 301 and the special frame 302 is calculated by the pixel value calculation section 401. As described above, the pixel value of the target pixel of the normal frame 301 and the pixel value of the target pixel of the special frame 302 are combined on the basis of a given computation.

During combining, the normal frame 301 and the special frame 302 are combined at a ratio based on the normal frame superimposition ratio 305. Such a combining process allows for the pixel value of the superimposed frame 303 corresponding to the target pixel to be calculated.

In step S105, it is determined whether or not all the pixels have been processed. In the case where it is determined in step S105 that not all the pixels have been processed, the process proceeds to step S106, and the next pixel is a target pixel. Then, the processes from step S103 onward are repeated for the new target pixel.

On the other hand, in a case where it is determined in step S105 that all the pixels have been processed, the process proceeds to step S107, and the next frame is a target frame, and the processes from step S102 onward are repeated for the new target frame.

As described above, superimposition is carried out at an appropriate superimposition ratio on a pixel-by-pixel basis. Therefore, the present technology can present, to the user, a superimposed image that permits accurate confirmation of an area emitting fluorescence without losing detailed information regarding the fluorescence-emitting area, for example, during observation of a special image such as fluorescence image.

Also, it is possible to present, to the user, a superimposed image that permits accurate confirmation of information regarding a periphery of a fluorescence-emitting area without losing such information.

Because the above have been made possible, it is possible to confirm, for example, the positions of blood vessels, lymphatic vessels, lymphatic nodes, biliary tracts, urinary tracts, and lesions with more accuracy, thus providing advantageous effects such as improved surgical precision and reduced surgery time.

<Recording Medium>

The series of processes described above may be performed by hardware or software. In the case where the series of processes are performed by software, the program included in the software is installed to a computer. Here, the computer includes not only a computer incorporated in dedicated hardware but also, for example, a general-purpose personal computer capable of performing a variety of functions when various programs are installed therein.

Figure 24:
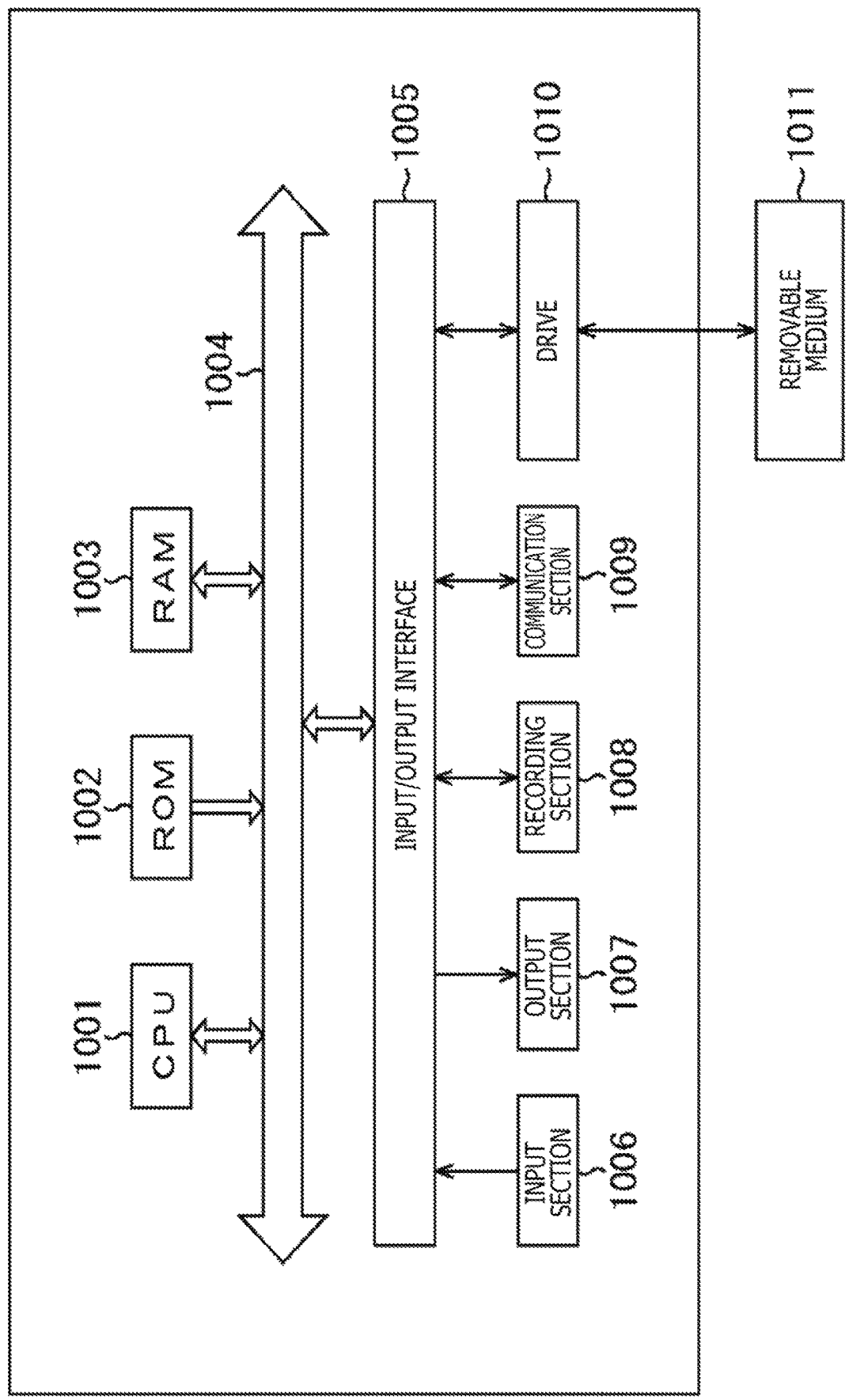
FIG. 24 is a diagram for describing a recording medium.

FIG. 24 is a block diagram illustrating a hardware configuration example of a computer for performing the above series of processes using the program. In a computer, a CPU (Central Processing Unit) 1001, a ROM (Read Only Memory) 1002, and a RAM (Random Access Memory) 1003 are connected to each other by a bus 1004. An input/output interface 1005 is further connected to the bus 1004. An input section 1006, an output section 1007, a storage section 1008, a communication section 1009, and a drive 1010 are connected to the input/output interface 1005.

The input section 1006 includes a keyboard, a mouse, a microphone, and so on. The output section 1007 includes a display, a speaker, and so on. The storage section 1008 includes a hard disk, a non-volatile memory, and so on. The communication section 1009 includes a network interface and so on. The drive 1010 drives a removable medium 1011 such as magnetic disk, optical disc, magneto-optical disk, or semiconductor memory.

In the computer thus configured, the CPU 1001 loads, for example, the program stored in the storage section 1008 into the RAM 1003 via the input/output interface 1005 and the bus 1004 for execution, thereby allowing the above series of processes to be performed.

The program executed by the computer (CPU 1001) can be provided recorded, for example, in the removable medium 1011 as a packaged medium or the like. Alternatively, the program can be provided via a wired or wireless transport medium such as local area network, the Internet, and digital satellite broadcasting.

In the computer, the program can be installed to the storage section 1008 via the input/output interface 1005 by inserting the removable medium 1011 into the drive 1010. Alternatively, the program can be received by the communication section 1009 via a wired or wireless transport medium and installed to the storage section 1008. In addition to the above, the program can be installed, in advance, to the ROM 1002 or the storage section 1008.

It should be noted that the program executed by the computer may perform the processes chronologically in accordance with a sequence described in the present specification. Alternatively, the program may perform the processes in parallel or when necessary as when the program is invoked.

In the present specification, the term "system" refers to an apparatus as a whole that includes a plurality of apparatuses.

It should be noted that the effects described in the present specification are merely illustrative and are not limited and that there may be other effects.

It should be noted that embodiments of the present technology are not limited to those described above and can be modified in various ways without departing from the gist of the present technology.

It should be noted that the present technology can also have the following configurations:

(1)

A medical image processing apparatus including:

an acquisition section configured to acquire a normal frame captured with normal light irradiated on a subject and a special frame captured with special light irradiated on the subject;

a superimposition ratio calculation section configured to calculate, on the basis of an intensity value of the special frame, a superimposition ratio indicating a ratio at which the normal frame and the special frame are superimposed; and a superimposition processing section configured to perform a superimposition process of superimposing the normal frame and the special frame on the basis of the superimposition ratio.

(2)

The medical image processing apparatus according to feature (1), in which in a case where the intensity value of the special frame is large, the superimposition ratio of the special frame is set high, and in which in a case where the intensity value of the special frame is small, the superimposition ratio of the special frame is set low.

(3)

The medical image processing apparatus according to feature (1) or (2), in which first and second thresholds are set within a range of values that can be taken on by the intensity value, in which in a case where the intensity value is smaller than the first threshold, the superimposition ratio of the normal frame is set higher than the superimposition ratio of the special frame, and in which in a case where the intensity value is larger than the second threshold, the superimposition ratio of the normal frame is set lower than the superimposition ratio of the special frame.

(4)

The medical image processing apparatus according to feature (3), in which in a case where a subject is captured that causes a maximum value that can be taken on by the intensity value of the special frame to decrease, the second threshold is set to a small value.

(5)

The medical image processing apparatus according to feature (3) or (4), in which in a case where it is desirable to reduce an effect of a minute signal of the special frame, the first threshold is set to a large value.

(6)

The medical image processing apparatus according to any one of features (1) to (5), in which third and fourth thresholds are set within a range of values that can be taken on by the superimposition ratio of the normal frame, in which the third threshold is applied as the superimposition ratio of the normal frame when the intensity value is small, and in which the fourth threshold is applied as the superimposition ratio of the normal frame when the intensity value is large.

(7)

The medical image processing apparatus according to feature (6), in which in a case where a subject is captured that causes a maximum value that can be taken on by the intensity value of the special frame to decrease, the fourth threshold is set to a small value.

(8)

The medical image processing apparatus according to feature (6) or (7), in which in a case where it is desirable to reduce an effect of a minute signal of the special frame, the third threshold is set to a large value.

(9)

The medical image processing apparatus according to any one of features (1) to (8), in which the first and second thresholds are set within the range of values that can be taken on by the intensity value, in which the third and fourth thresholds are set within the range of values that can be taken on by the superimposition ratio of the normal frame, and in which the first to fourth thresholds are set to values suitable for the subject, which is an observation target.

(10)

The medical image processing apparatus according to feature (9), in which the superimposition ratio calculation section calculates the superimposition ratio by using the first to fourth thresholds.

(11)

The medical image processing apparatus according to feature (9), in which the superimposition ratio calculation section calculates the superimposition ratio by using a function defined by the first to fourth thresholds.

(12)

The medical image processing apparatus according to feature (9), in which
in a case where a purpose of use is to clearly determine whether or not light emission occurs as a result of irradiation of special light in the special frame, the first and third thresholds are set to large values, and the second and fourth threshold are set to small values.

(13)

A medical image processing method including:
a step in which a normal frame captured with normal light irradiated on a subject and a special frame captured with special light irradiated on the subject are acquired;
a step in which a superimposition ratio indicating a ratio at which the normal frame and the special frame are superimposed is calculated on the basis of an intensity value of the special frame; and
a step in which a superimposition process of superimposing the normal frame and the special frame is performed on a basis of the superimposition ratio.

(14)

A program for causing a computer to perform processes including:
a step in which a normal frame captured with normal light irradiated on a subject and a special frame captured with special light irradiated on the subject are acquired;
a step in which a superimposition ratio indicating a ratio at which the normal frame and the special frame are superimposed is calculated on the basis of an intensity value of the special frame; and
a step in which a superimposition process of superimposing the normal frame and the special frame is performed on a basis of the superimposition ratio.

REFERENCE SIGNS LIST

110 Endoscopic apparatus, 111 Light source section, 112 Imaging section, 113 Development section, 114 Image processing section, 115 Display section, 121 Switching section, 122 Motion vector detection section, 123 Correction amount estimation section, 124 Frame memory, 125 Motion correction section, 126 Superimposition processing section, 131, 132 Frame memories, 133 Frame selection section, 134 Block matching section, 135 Vector correction section, 401 Pixel value calculation section, 402 Normal frame superimposition ratio calculation section.

The invention claimed is:

1. A medical image processing apparatus comprising:
circuitry configured to
acquire a normal frame captured with normal light irradiated on a subject and a special frame captured with special light irradiated on the subject;
calculate, on a basis of an intensity value of the special frame, a superimposition ratio indicating a ratio at which the normal frame and the special frame are superimposed; and
superimpose the normal frame and the special frame on a basis of the superimposition ratio, wherein
first and second thresholds are set within a range of values that can be taken on by the intensity value, wherein
in a case where the intensity value is smaller than the first threshold, the superimposition ratio of the normal frame is set higher than the superimposition ratio of the special frame, and wherein
in a case where the intensity value is larger than the second threshold, the superimposition ratio of the normal frame is set lower than the superimposition ratio of the special frame.

2. A medical image processing method comprising:
capturing a normal frame with normal light irradiated on a subject and a special frame with special light irradiated on the subject;
calculating a superimposition ratio indicating a ratio at which the normal frame and the special frame are superimposed on a basis of an intensity value of the special frame;
superimposing the normal frame and the special frame on a basis of the superimposition ratio;
setting first and second threshold within a range of values that can be taken on by the superimposition ratio of the normal frame;
applying the first threshold as the superimposition ratio of the normal frame when the intensity value is small; and
applying the second threshold as the superimposition ratio of the normal frame when the intensity value is large.

3. A program stored on a non-transitory computer-readable storage medium for causing a computer to perform processes comprising:
capturing a normal frame with normal light irradiated on a subject and a special frame with special light irradiated on the subject;
calculating a superimposition ratio indicating a ratio at which the normal frame and the special frame are superimposed on a basis of an intensity value of the special frame;
superimposing the normal frame and the special frame on a basis of the superimposition ratio;
setting first and second thresholds within a range of values that can be taken on by the intensity value;
setting third and fourth thresholds within the range of values that can be taken on by the superimposition ratio of the normal frame; and
setting the first to fourth thresholds to values suitable for the subject, which is an observation target.

4. The medical image processing apparatus according to claim 1, wherein
in a case where the intensity value of the special frame is large, the superimposition ratio of the special frame is set high, and wherein
in a case where the intensity value of the special frame is small, the superimposition ratio of the special frame is set low.

5. The medical image processing apparatus according to claim 1, wherein
in a case where a subject is captured that causes a maximum value that can be taken on by the intensity value of the special frame to decrease, the second threshold is set to a small value.

6. The medical image processing apparatus according to claim 1, wherein
to reduce an effect of a minute signal of the special frame, the first threshold is set to a large value.

7. The medical image processing method according to claim 2, wherein
in a case where a subject is captured that causes a maximum value that can be taken on by the intensity value of the special frame to decrease, the second threshold is set to a small value.

8. The medical image processing method according to claim 2, wherein to reduce an effect of a minute signal of the special frame, the first threshold is set to a large value.

9. The program according to claim 3, wherein the computer is to perform processes further comprising:
   calculating the superimposition ratio by using the first to fourth thresholds.

10. The program according to claim 3, wherein the computer is to perform processes further comprising:
    calculating the superimposition ratio using a function defined by the first to fourth thresholds.

11. The program according to claim 3, wherein the computer is to perform processes further comprising:
    in a case where a purpose of use is to clearly determine whether or not light emission occurs as a result of irradiation of special light in the special frame, setting the first and third thresholds to large values, and setting the second and fourth threshold to small values.

12. The medical image processing apparatus according to claim 1, wherein the circuitry is configured to calculate the superimposition ratio and superimpose the normal frame and the special frame on a pixel-by-pixel basis.

13. The medical image processing method according to claim 2, wherein calculating the superimposition ratio and superimposing the normal frame and the special frame are on a pixel-by-pixel basis.

14. The program according to claim 3, wherein calculating the superimposition ratio and superimposing the normal frame and the special frame are on a pixel-by-pixel basis.

* * * * *